United States Patent
Bohlin et al.

(10) Patent No.: US 9,701,649 B2
(45) Date of Patent: *Jul. 11, 2017

(54) CRYSTAL MODIFICATIONS OF ELOBIXIBAT

(71) Applicant: Elobix AB, Gothenburg (SE)

(72) Inventors: Martin Bohlin, Johanneshov (SE);
Erica Tjerneld, Enskede (SE);
Andreas Vestermark, Stockholm (SE);
Ingvar Ymen, Saltsjo-boo (SE)

(73) Assignee: Elobix AB, Gothenburg (SE)

( * ) Notice: Subject to any disclaimer, the term of this patent is extended or adjusted under 35 U.S.C. 154(b) by 0 days.

This patent is subject to a terminal disclaimer.

(21) Appl. No.: 15/134,583

(22) Filed: Apr. 21, 2016

(65) Prior Publication Data

US 2016/0237049 A1 Aug. 18, 2016

Related U.S. Application Data

(63) Continuation of application No. 14/920,080, filed on Oct. 22, 2015, now Pat. No. 9,409,875, which is a continuation of application No. PCT/EP2014/058432, filed on Apr. 25, 2014.

(30) Foreign Application Priority Data

Apr. 26, 2013 (SE) ........................ 1350517

(51) Int. Cl.
*C07D 281/10* (2006.01)
*A61K 31/554* (2006.01)
*C07D 281/02* (2006.01)

(52) U.S. Cl.
CPC .......... *C07D 281/10* (2013.01); *A61K 31/554* (2013.01); *C07D 281/02* (2013.01); *C07B 2200/13* (2013.01)

(58) Field of Classification Search
CPC ........................ C07D 281/10; A61K 31/554
USPC ..................... 540/552; 514/211.09
See application file for complete search history.

(56) References Cited

U.S. PATENT DOCUMENTS

| | | | |
|---|---|---|---|
| 4,507,235 A | 3/1985 | Wunsch | |
| 5,422,124 A | 6/1995 | Valducci | |
| 5,811,388 A | 9/1998 | Friend et al. | |
| 5,994,391 A | 11/1999 | Lee et al. | |
| 6,069,167 A | 5/2000 | Sokol | |
| 6,277,831 B1 | 8/2001 | Frick et al. | |
| 6,346,527 B1 | 2/2002 | Takenaka et al. | |
| 6,355,672 B1 | 3/2002 | Yasuma et al. | |
| 6,387,924 B2 | 5/2002 | Lee et al. | |
| 6,387,944 B1 | 5/2002 | Frick et al. | |
| 6,676,979 B2 | 1/2004 | Marlett et al. | |
| 6,906,058 B2 | 6/2005 | Starke et al. | |
| 6,943,189 B2 | 9/2005 | Keller et al. | |
| 7,019,023 B2 | 3/2006 | Frick et al. | |
| 7,125,864 B2 | 10/2006 | Starke et al. | |
| 7,132,416 B2 | 11/2006 | Starke et al. | |
| 7,132,557 B2 | 11/2006 | Wilkes et al. | |
| 7,192,945 B2 | 3/2007 | Starke et al. | |
| 7,192,946 B2 | 3/2007 | Starke et al. | |
| 7,192,947 B2 | 3/2007 | Starke et al. | |
| 7,226,943 B2 | 6/2007 | Starke et al. | |
| 7,238,684 B2 | 7/2007 | Starke et al. | |
| 7,514,421 B2 | 4/2009 | Abrahamsson et al. | |
| 8,067,584 B2 | 11/2011 | Starke et al. | |
| 9,409,875 B2 * | 8/2016 | Bohlin ................ | C07D 281/10 |
| 2002/0142054 A1 | 10/2002 | Marlett et al. | |
| 2003/0125316 A1 | 7/2003 | Keller et al. | |
| 2003/0143183 A1 | 7/2003 | Knudsen et al. | |
| 2003/0215843 A1 | 11/2003 | Poupon et al. | |
| 2004/0067933 A1 | 4/2004 | Starke et al. | |
| 2005/0009805 A1 | 1/2005 | Sasahara et al. | |
| 2005/0113362 A1 | 5/2005 | Lindstedt et al. | |
| 2005/0124557 A1 | 6/2005 | Lindqvist | |
| 2005/0171204 A1 | 8/2005 | Lindstedt et al. | |
| 2005/0197376 A1 | 9/2005 | Kayakiri et al. | |
| 2005/0282822 A1 | 12/2005 | Alstermark et al. | |
| 2006/0083790 A1 | 4/2006 | Anderberg et al. | |
| 2007/0197522 A1 | 8/2007 | Edwards et al. | |
| 2008/0300171 A1 | 12/2008 | Balkan et al. | |
| 2009/0131395 A1 | 5/2009 | Antonelli et al. | |

(Continued)

FOREIGN PATENT DOCUMENTS

| | | |
|---|---|---|
| DE | 19825804 | 8/2000 |
| EP | 0489423 | 12/1991 |
| EP | 0372542 | 10/1992 |
| EP | 0573848 | 5/1993 |
| EP | 0549967 | 7/1993 |
| EP | 0624593 | 11/1994 |
| EP | 0624594 | 11/1994 |
| EP | 0624595 | 11/1994 |
| EP | 0624596 | 11/1994 |
| EP | 0864582 | 9/1998 |

(Continued)

OTHER PUBLICATIONS

"A Long-Term, Open-Label Study of LUM001 With a Double-Blind, Placebo Controlled, Randomized Drug Withdrawal Period to Evaluate Safety and Efficacy in Children With Alagille Syndrome (ICONIC)," Clinical Trials.gov, Jun. 9, 2014, retrieved Oct. 3, 2014, http://clinicaltrials.gov/ct2/show/NCT02160782?term=LUM001& rank=7, 4 pages.

(Continued)

*Primary Examiner* — Deepak Rao
(74) *Attorney, Agent, or Firm* — Fish & Richardson P.C.

(57) ABSTRACT

The present invention relates to crystal modifications of N-{(2R)-2-[({[3,3-dibutyl-7-(methyl-thio)-1,1-dioxido-5-phenyl-2,3,4,5-tetrahydro-1,5-benzothiazepin-8-yl]oxy}acetyl)amino]-2-phenylethanolyl}glycine (elobixibat), more specifically crystal modifications I, IV, MeOH-1, EtOH-1, 1-PrOH-1 and 2-PrOH-1. The invention also relates to a process for the preparation of these crystal modifications and to a pharmaceutical composition comprising crystal modification IV.

12 Claims, 22 Drawing Sheets

(56) References Cited

U.S. PATENT DOCUMENTS

| | | | |
|---|---|---|---|
| 2010/0130472 A1 | 5/2010 | Young et al. | |
| 2010/0286122 A1 | 11/2010 | Belyk | |
| 2011/0294767 A1 | 12/2011 | Gedulin et al. | |
| 2012/0114588 A1 | 5/2012 | Starke et al. | |
| 2012/0157399 A1 | 6/2012 | Young et al. | |
| 2013/0029938 A1 | 1/2013 | Aquino et al. | |
| 2013/0059807 A1 | 3/2013 | Gedulin et al. | |
| 2013/0108573 A1 | 5/2013 | Gedulin et al. | |
| 2013/0109671 A1 | 5/2013 | Gedulin et al. | |
| 2013/0225511 A1* | 8/2013 | Gillberg | A61K 31/554 514/21.91 |
| 2013/0236541 A1* | 9/2013 | Gillberg | A61K 31/554 424/463 |
| 2015/0031636 A1* | 1/2015 | Gillberg | A61K 31/554 514/21.91 |
| 2015/0031637 A1* | 1/2015 | Gillberg | A61K 31/554 514/21.91 |
| 2016/0039777 A1 | 2/2016 | Bohlin et al. | |
| 2016/0193277 A1* | 7/2016 | Gillberg | A61K 31/554 514/21.91 |
| 2016/0194353 A1* | 7/2016 | Gillberg | A61K 31/554 514/21.91 |
| 2016/0229822 A1* | 8/2016 | Bohlin | C07D 281/10 |

FOREIGN PATENT DOCUMENTS

| | | |
|---|---|---|
| EP | 1173205 | 4/2000 |
| EP | 1535913 | 6/2005 |
| EP | 1719768 | 11/2006 |
| GB | 2262888 | 7/1996 |
| WO | WO 93/16055 | 8/1993 |
| WO | WO 94/18183 | 8/1994 |
| WO | WO 94/18184 | 8/1994 |
| WO | WO 96/05188 | 2/1996 |
| WO | WO 96/08484 | 3/1996 |
| WO | WO 96/16051 | 5/1996 |
| WO | WO 97/33882 | 9/1997 |
| WO | WO 98/03818 | 1/1998 |
| WO | WO 98/07449 | 1/1998 |
| WO | WO 98/38182 | 9/1998 |
| WO | WO 98/40375 | 9/1998 |
| WO | WO 99/01149 | 1/1999 |
| WO | WO 99/32478 | 1/1999 |
| WO | WO 99/35135 | 7/1999 |
| WO | WO 99/64409 | 7/1999 |
| WO | WO 99/64410 | 12/1999 |
| WO | WO 00/01687 | 1/2000 |
| WO | WO 00/38725 | 7/2000 |
| WO | WO 00/38726 | 7/2000 |
| WO | WO 00/38727 | 7/2000 |
| WO | WO 00/38728 | 7/2000 |
| WO | WO 00/38729 | 7/2000 |
| WO | WO 00/47568 | 8/2000 |
| WO | WO 00/61568 | 10/2000 |
| WO | WO 00/62810 | 10/2000 |
| WO | WO 01/60807 | 8/2001 |
| WO | WO 01/66533 | 9/2001 |
| WO | WO 01/68096 | 9/2001 |
| WO | WO 01/68637 | 9/2001 |
| WO | WO 02/08211 | 1/2002 |
| WO | WO 02/32428 | 4/2002 |
| WO | WO 02/50051 | 6/2002 |
| WO | WO 02/53548 | 6/2002 |
| WO | WO 03/020710 | 3/2003 |
| WO | WO 03/022286 | 3/2003 |
| WO | WO 03/022804 | 3/2003 |
| WO | WO 03/022825 | 3/2003 |
| WO | WO 03/022830 | 3/2003 |
| WO | WO 03/051821 | 6/2003 |
| WO | WO 03/051822 | 6/2003 |
| WO | WO 03/061663 | 7/2003 |
| WO | WO 03/091232 | 11/2003 |
| WO | WO 03/106482 | 11/2003 |
| WO | WO 2004/006899 | 1/2004 |
| WO | WO 2004/056748 | 7/2004 |
| WO | WO 2004/076430 | 9/2004 |
| WO | WO 2004/089350 | 9/2004 |
| WO | WO 2004/020421 | 10/2004 |
| WO | WO 2007/009655 | 1/2007 |
| WO | WO 2007/009656 | 1/2007 |
| WO | WO 2008/058628 | 5/2008 |
| WO | WO 2008/058630 | 5/2008 |
| WO | WO 2008/058631 | 5/2008 |
| WO | WO 2010/062861 | 6/2010 |
| WO | WO 2011/137135 | 11/2011 |
| WO | WO 2011/150286 | 11/2011 |
| WO | WO 2012/064267 | 5/2012 |
| WO | WO 2012/064268 | 5/2012 |
| WO | WO 2013/063512 | 5/2013 |
| WO | WO 2013/063526 | 5/2013 |

OTHER PUBLICATIONS

"Alagile Syndrome," Wikipedia, the free encyclopedia, posted on or about Feb. 11, 2005, retrieved Feb. 12, 2014, http://en.wikipedia.org/wiki/Alagille_syndrome, 3 pages.

"Albireo's Lead Compound in Cholestatic Liver Diseases, A4250, Projects Against Bile Acid-Mediated Cholestatic Liver Injury in Mice," Albireo Press Release, Apr. 11, 2014, 2 pages.

"An Extension Study to Evaluate the Long-Term Safety and Durability of Effect of LUM001 in the Treatment of Cholestatic Liver Disease in Subjects With Alagille Syndrome (IMAGINE)," Clinical Trials.gov, Jan. 23, 2014, retrieved on Oct. 3, 2014, http://clinicaltrials.gov/ct2/show/NCT02047318?term=LUM001&rank=3, 3 pages.

"An Extension Study to Evaluate the Long-Term Safety and Durability of Effect of LUM001 in the Treatment of Cholestatic Liver Disease in Subjects With Alagille Syndrome (IMAGINE-II)," Clincal Trials.gov, Apr. 16, 2014, retrieved on Oct. 3, 2014, http://clinicaltrials.gov/ct2/show/NCT02117713?term=LUM001&rank=2, 3 pages.

"Bowel Diversion Surgeries: Ileostomy, Colostomy, Ileoanal Reservoir and Continent Ileostomy," US Department of Health and Human Services: National Institute of Diabetes and Digestive and Kidney Diseases, Feb. 2009, retrieved on Jan. 27, 2014, http://digestive.niddk.nih.gov/ddiseases/pub/ileostomy/Bowel_Diversion_508.pdf, 4 pages.

"EASL Clinical Practice Guidelines: Management of cholestatic liver diseases," European Assoc. for the Study of the Liver, Journal of Hepatology, 2009, 51:237-267.

"Evaluation of LUM001 in the Reduction of Pruritus in Alagille Syndrome (ITCH)," Clinical Trials.gov, Feb. 5, 2014, retrieved on Oct. 3, 2014, http://clinicaltrials.gov/ct2/show/NCT02057692?term=LUM001&rank=5, 4 pages.

"IBAT inhibitor A4250 for Cholestatic Pruritus," ClinicalTrials.gov, Last updated Feb. 10, 2015, https://clinicaltrials.gov/ct2/show/NCT02360852?term=a4250&rank=1, 3 pages.

"Initiation of a Phase II Trial for A4250, the Company's Lead Compound for Cholestatic Liver Diseases and NASH," Albireo Pharma Press Release, Feb. 5, 2015, http://www.alberiopharma.com/News.aspx?PageID=1600872, 2 pages.

"Lumena Pharmaceuticals Now Dosing Patients in the INDIGO Phase 2 Clinical Trial of LUM001 in Pediatric Patients with Progressive Familial Intrahepatic Cholestasis," PR Newswire, May 9, 2014, retrieved on Oct. 3, 2014, http://www.prnewswire.com/news-releases/lumena-pharmaceuticals-now-dosing-patients-in-the-indigo-phase-2-clinical-trial-of-lum001-in-pediatric-patients-with-progressive-familial-intrahepatic-cholestasis-258609691.html, 3 pages.

"Open Label Study to Evaluate Efficacy and Long Term Safety of LUM001 in the Treatment of Cholestatic Liver Disease in Patients With Progressive Familial Intrahepatic Cholestasis (INDIGO)," Clinical Trials.gov, Feb. 5, 2014, retrieved on Oct. 3, 2014, http://clinicaltrials.gov/ct2/show/NCT02057718?term=LUM001&rank=4, 3 pages.

(56) References Cited

OTHER PUBLICATIONS

"Open Label Study to Evaluate Safety and Efficacy of LUM001 in Patients With Primary Sclerosing Cholangitis (CAMEO)," Clinical Trials.gov, Feb. 11, 2014, retrieved Oct. 3, 2014, http://clinicaltrials.gov/ct2/show/NCT02061540?term=LUM001&rank=6, 3 pages.
"Phase 2 Study to Evaluate LUM001 in Combination With Ursodeoxycholic Acid in Patients With Primary Biliary Cirrhosis (CLARITY)," Clinical Trials.gov, Jul. 17, 2013, retrieved Oct. 3, 2014, http://clinicaltrials.gov/ct2/show/NCT01904058?term=LUM001&rank=8, 3 pages.
"Progressive familial intrahepatic cholestasis," Wikipedia, the free encyclopedia, posted on or about Feb. 24, 2006, http://en.wikipedia.org/wiki/Progressive_familial_intrahepatic_cholestasis, 3 pages.
"Safety and Efficacy Study of LUM001 in the Treatment of Cholestatic Liver Disease in Patients With Alagille Syndrome (IMAGO)," Clinical Trials.gov, Jul. 16, 2013, http://clinicaltrials.gov/ct2/show/NCT01903460?term=LUM001&rank=1, 3 pages.
"What is Alagille Syndrome?," European Medicines Agency, Jan. 21, 2014, retrieved on Oct. 3, 2014, http://www.ema.europa.eu/docs/en_GB/document_library/Orphan_designation/2014/01/WC500159874.pdf, 6 pages.
Alissa et al., "Invited Review: Update on Progressive Familial Intrahepatic Cholestasis," *Journal of Pediatric Gastroenterology and Nutrition*, 2008, 46:241-252.
American Diabetes Association, "Management of Dyslipidemia in Adults with Diabetes," Diabetes Care, Jan. 2003, 26(1).
Angulo, "Use of ursodeoxycholic acid in patients with liver disease," *Current Gastroenterology Reports*, Feb. 1, 2002, 4(1):37-44.
Artursson and Karlsson, "Corresslation Between Oral Drug Absorption in Humans and Apparent Drug Permeability Coefficients in Human Intestinal Epithelial (CACO-2) Cells," Biochemical and Biophysical Research Communications, Mar. 1991, 175(3):880-885.
Attili et al., "Bile Acid-induced Liver Toxicity: Relation to the Hydrophobic-Hydrophilic Balance of Bile Acids," Medical Hypotheses, 1986, 19:57-69.
Baghdasaryan et al , "Inhibition of intestinal bile acid absorption by ASBT inhibito A4250 protects against bile acid-mediated cholestatic liver injury in mice," J. Hepatology, 2014, 60:S57.
Baghdasaryan et al., "Inhibition of intestinal bile acid absorption by ASBT inhibito A4250 protects against bile acid-mediated cholestatic liver injury in mice," Presented at the EASL Conference, London, UK, Apr. 12, 2015, http://www.albireopharma.com/News.aspx?PageID=1591817, 22 pages.
Bajor et al., "Bile acids: short and long term effects in the intestine," Scandanavian J. Gastro., 2010, 45:645-664.
Banker et al., "Modern Pharmaceutics, 3ed", Marcel Dekker, New York, 1996, pp. 451 and 596.
Board of Appeal of European Patent Office, Case No. T 077/08-3.3.01, dated May 24, 2011, 17 pages.
Bonge et al., "Cytostar-T Scintillating Microplate Assay for Measurement of Sodium-Dependent Bile Acid Uptake in Transfected HEK-293 Cells," Analytical Biochemistry, 2000, 282:94-101.
Brunzell and Hokanson, "Dislipidemia of Central Obesity and Insulin Resistance," Diabetes Care, 1999, 22(Suppl. 3):C10-C13.
Byrn et al., "Pharmaceutical Solids: A Strategic Approach to Regulatory Considerations," Pharmaceutical Research, 1995, 12(7), pp. 945-954.
Chen et al , "Inhibition of apical sodium-dependent bile acid transporter as a novel treatment for diabetes," Am J Physiol Endocrinol Metab, 2012, 302:E68-E76.
Chen et al., "Progressive Familial Intrahepatic Cholestasis, Type 1, Is Associated with Decreased Farnesoid X Receptor Activity," Gastroenterology, 2004, 126:756-764.
Chey et al., "A Randomized Placebo-Controlled Phase II b Trial of A3309, A Bile Acid Transporter Inhibitor, for Chronic Idiopathic Constipation," Am. J. Gastroenterology, May 2011, 106:1803-1812.
Dashti et al., "A Phospholipidomic Analysis of All Defined Human Plasma Lipoproteins," Nature.com: Scientific Reports, Nov. 2011, DOI: 10.1038, 11 pages.
Davit_Spraul et al., "ATP8B1 and ABCB11 Analysis in 62 Children with Normal Gamma-Glutamyl Transferase Progressive Familial Intrahepatic Cholestasis (PFIC): Phenotypic Differences Between PFIC1 and PFIC2 and Natural History," *Hepatology: Autoimmune, Cholestatic and Biliary Disease*, May 2010, 1645-1655.
Davit-Spraul et al., "Progressive familial intrahepatic cholestasis," *Orphanet Journal of Rare Diseases*, Jan. 2009, 4:1-12.
Dawson et al., "Bile acid transporters" J. Lipid Res. 2009, 50, 2340-2357.
DeFronzo et al., "Insuline resistance, A multisurfaced syndrome responsible for NIDDM, obesity, hypertension, dyslipidemia and atherosclerotic cardiovascular disease," Diabetes Care, 1991, 14:173-194.
Di Padova et al., "Double-blind placebo-controlled clinical trial of microporous chlestyramine in the treatment of intra- and extra-hepatic cholestasis: relationship between itching and serum bile acids," Methods Find Exp Clin Pharmacol., Dec. 1984, 6(12):773-776 (Abstract Only).
Dongiovanni et al., "Genetic Predisposition in NAFLD and NASH: Impact on Severity of Liver Disease and Response to Treatment," Curren Pharma Design, 2013, 19:5219-5238.
Espenshade and Hughes, "Regulation of Sterol Synthesis in Eukaryotes," Annu. Rev. Genet., 2007, 41:401-427.
Extended European Search Report in European Application No. 11840392 2, mailed Feb. 24, 2014, 7 pages.
Extended European Search Report in European Application No. 11840481.3, mailed Feb. 13, 2014, 10 pages.
Gibney, "Shire Reports Topline Results from First of Three Placebo-Controlled Phase 2 Studies of SHP625 (LUM001) in Children with Alagille Syndrome," FierceBiotech.com, Apr. 9, 2015, http://www.firecebiotech.com/node/443176/print, 3 pages.
Gillberg et al., "The IBAT Inhibition by A3309—A Potential Mechanism for the Treatment of Constipation," Gastroenterology, 2010, 138(5), Supp 1, S-224.
Glasgov et al., "Compensatory enlargement of human athersclerotic coronary arteries," N Engl. J. Med., May 1987, 316(22):1371-1375 (Abstract Only).
Govers et al., "Characterization of the adsorption of conjugated and unconjugated bile acids to insoluble, amorphous calcium phosphate", Journal of Lipid Research 35(5):741-748, 1994.
Heathcote, "Management of primary biliary cirrhosis," Hepatology, 2000, 31(4):1005-1013.
Higaki et al , "Inhibition of ileal na+/bile acid cotranporter by S-8921 reduces serum cholesteral and prevents atherosclerosis in rabbits", Arteriosclerosis, Thrombosis, and Vascular Biology 18(8):1304-1311, 1998.
Huang et al., "Discovery of Potent, Nonsystemic Apical Sodium-Codependent Bile Acid Transporter Inhibitors (Part 2)," J. Med. Chem., 2005, 48:5853-5868.
International Preliminary Report on Patentability for International Application No. PCT/SE2011/051335, mailed May 23, 2011, 7 pages.
International Preliminary Report on Patentability for International Application No. PCT/SE2011/051336, mailed May 23, 2013, 11 pages.
International Search Report and Written Opinion for Application No. PCT/EP2014/058432, issued Jul. 11, 2014, 9 pages.
International Search Report and Written Opinion for International Application No. PCT/SE2011/051335, mailed Feb. 3, 2012, 12pages.
International Search Report and Written Opinion for International Application No. PCT/SE2011/051336, mailed Feb. 22, 2012, 18 pages.
Ishibashi et al., "Hypercholesterolemia in low density lipoprotein receptor knockout mice and its reversal by adenovirus-mediated gene delivery", Journal of Clinical Investigation 92(2):883-893, 1993.
Jacquet et al., "Alagille Syndrome in Adult Patients: It is Never Too Late," *American Journal of Kidney Diseases*, May 2007, 49(5):705-709.

(56) References Cited

OTHER PUBLICATIONS

Korman et al., "Assessment of Activity in Chronic Active Liver Disease," New England Journal of Medicine, 2010, 290(25):1399-1402.
Kumar and Tandon, "Use of ursodeoxycholic acid in liver diseases," J. Gastroenterology and Hepatology, 2001, 16:3-14.
Kurata et al., "A novel class of apical sodium-dependent bile acid transporter inhibitors: the amphiphilic 4-oxo-1-phenyl-1,4-dihydroquinoline derivatives," Bioorganic & Medicinal Chemistry Letters, 2004, 14:1183-1186.
Lanzini et al., "Intestinal absorption of the bile acid analogue $^{75}$Se-homocholic acid-taurine is increased in primary biliary cirrhosis and reverts to normal during ursodeoycholic acid administrations," Gut, 2003, 52:1371-1375.
Lewis et al., "Effects of 2164U90 on ileal bile acid adsorption and serum cholesterol in rats and mice", Journal of Lipid Research 36(5):1098-1105, 1995.
Ling, "Congenital cholestatic syndromes: What happens when children grow up?," Can J Gastroenterol, Nov. 11, 2007, 21(11):743-751.
Longo et al., "Hyperlipidemia in chronic cholestatic liver disease," Curr. Treat. Options Gastrenterol., 2001, 4:111-114.
Lykavieris et al., "Outcome of liver disease in children with Alagille syndrome: a study of 163 patients," *Gut*, 2001, 49:431-435.
MerckManuals.com', "Obesity," 2008, Merch Manual for Health Care Professionals, Section-Nutritional Disorders, Chapter—"Obesity and the metabolic syndrome," retrieved on Feb. 22, 2012, http://www.merchmanuals.com/professional/nutritional_disorders/obesity_and_the_metabolic_syndrome/metabolic_syndrome.html?qt=metabolicsyndrome&alt=sh, 10 pages.
Morissette et al., "High-throughput crystallization: polymorphs, salts, co-crystals and solvates of pharmaceutical solids," Advanced Drug Delivery Reviews, 2004, 56:275-300.
Nagase et al., "Preparation of Benzothiazepine derivatives with activity of brining about high blood GLP-1 concentration," CAPLUS Database, Jul. 2002, retrieved from STN Database on Mar. 31, 2014, https://stneasy.cas.org/tmp/20140331/443268-0025347726-200/349520738.html, 2 pages.
Parker et al., "Molecular mechanisms underlying bile acid-stimulated glucagon-like peptide-1 secretion," British J. Pharmacology, 2012, 165:414-423.
Patani et al., "Bioisosterism: A Rational Approach in Drug Design," Chem Rev, 1996, 96:3147-3176.
Plump et al., "Severe hypercholesterolemia and atherosclerosis in apolipoprotein E-deficient mice created by homologous recombination in ES cells", Cell (71):343-353, 1992.
Podesta et al., "Treatment of pruritus of primary biliary cirrhosis with rifampin," Dig. Dis. Sci, 1991, 36(2):216-220.
Poupon et al., "Chronic Cholestatic Disease," J. Hepatology, 2000, 32(1):12-140.
Schiller, "Review article: the therapy of constipation", Alimentary Pharmacology and Therapeutics 15(6):749-763, 2001.
Shah et al., "Role of Caco-2 Cell Monolayers in Prediction of Intestinal Drug Absortption," Biotechnol. Prog., 2006, 22:186-198.
Shang et al., "Colesevelam improves insulin resistance in a diet-induced obesity (F-DIO) rat model by increasing the release of GLP-1," Am J. Physiol Gastrointest Liver Physiol, 2010, 298:G419-G424.
Sorrentino et al., "A Clinical-Morphological Study on Cholestatic Presentation of Nonalcoholic Fatty Liver Disease," Digestive Disease and Sciences, Jun. 2005, 50(6):1130-1135.
Sprong et al., "Dietary Calcium Phosphate Promotes Listeria monosytogenes colonization and translocation in rats red diets containing corn oil but not milk fat1", J. Nutrition (US) 132(6):1269-1274, 2002.
Staels and Kuipers, "Bile Acid Sequestrants and the Treatment of Type 2 Diabetes Mellitus," Drugs, 2007, 67(10):1383-1392.
Stein, "Managing Dyslipidemia in the High-Risk Patient," Am J. Cardiol., 2002, 89:50-57.
Tanaka et al., "Genetic and Familial considerations of Primary Biliary Cirrhosis," Am. J. Gastroenterology, 2001, 96(1): 8-15.
Tollefson et al., "A novel class of apical sodium co-dependent bile acid transporter inhibitors: the 1,2-Benzothiazepines", Bioorganic and Medicinal Chemistry Letters 12:3727-3730, 2003.
Tremont et al., "Discovery of Potent, Nonsystemic Apical Sodium-Codependent Bile Acid Transporter Inhibitors (Part 1)," J. Med. Chem, 2005, 48:5837-5852.
Van Heek et al., "In vivo metabolism-based discovery of a potent cholesterol absorptions inhibitor, sch58235, in the rat and rhesus monkey through the identification of the active metabolites of sch48461," J. Pharmacol. Exp. Med, 1997, 283(1):157-163.
Van Tilberg et al., "Na+-dependent bile acid transport in the ileum: the balance between diarrhea and constipation", Gastroenterology 98(1):25-32, 1989.
Vippagunta et al., "Crystalline solids", Advanced Drug Delivery Reviews 48:3-26, 2001.
Watts and Illum, "Colonic Drug Delivery," Drug Development and Industrial Pharmacy, 1997, 23(9):893-913.
Welberg et al., "Calcium and the prevention of colon cancer", Scandinavian J. Gastroenterology Suppl. 188:52-59, 1991.
Williams et al., Foye's Principles of Medicinal Chemistry, 5th Edition, 2002, 59-63.
Wolff, "Burger's Medicinal Chemistry, 5ed, Part I", John Wiley & Sons, 1995, pp. 975-977.
Bavin, "Polymorphism in Process Development," Chemistry and Industry, 527-529, 1989.
Hancock et al., "Molecular Mobility of amorphous pharmaceutical solids below their glass transition temperatures," 12(6): 799-806, 1995.
Report filed at oral proceedings before opposition division, GMS-CFEP-2007-20, "Filtration and Drying Study on Amorphous and Form IV Atorvastatin Calcium," 2007.
Report EC20082069.02.01 dated Feb. 2009, filed with appellant's letter of Apr. 26, 2011.

\* cited by examiner

CRYSTAL MODIFICATIONS OF ELOBIXIBAT

CROSS-REFERENCE TO RELATED APPLICATIONS

This application is a continuation application of U.S. application Ser. No. 14/920,080, filed Oct. 22, 2015, which is a continuation application of and claims priority to International Application No. PCT/EP2014/058432, filed Apr. 25, 2014, which claims priority to SE 1350517-7, filed Apr. 26, 2013, each of which is incorporated by reference in its entirety herein.

The present invention relates to crystal modifications of N-{(2R)-2-[({[3,3-dibutyl-7-(methyl-thio)-1,1-dioxido-5-phenyl-2,3,4,5-tetrahydro-1,5-benzothiazepin-8-yl]oxy}acetyl)amino]-2-phenylethanolyl}glycine (elobixibat), more specifically crystal modifications I, IV, MeOH-1, EtOH-1, 1-PrOH-1 and 2-PrOH-1. The invention also relates to a process for the preparation of these crystal modifications and to a pharmaceutical composition comprising crystal modification IV.

BACKGROUND

WO 02/50051 discloses the compound 1,1-dioxo-3,3-dibutyl-5-phenyl-7-methylthio-8-(N-{(R)-1'-phenyl-1'-[N'-(carboxymethyl)carbamoyl]methyl}carbamoylmethoxy)-2,3,4,5-tetrahydro-1,5-benzothiazepine (elobixibat; IUPAC name: N-{(2R)-2-[({[3,3-dibutyl-7-(methylthio)-1,1-dioxido-5-phenyl-2,3,4,5-tetrahydro-1,5-benzothiazepin-8-yl]oxy}acetyl)amino]-2-phenyl-ethanolyl}glycine). This compound is an ileal bile acid transporter (IBAT) inhibitor, which can be used in the treatment or prevention of diseases such as dyslipidemia, constipation, diabetes and liver diseases. According to the experimental section of WO 02/50051, the last synthetic step in the preparation of elobixibat consists of the hydrolysis of a tert-butoxyl ester under acidic conditions. The crude compound was obtained by evaporation of the reaction mixture under reduced pressure and purification of the residue by preparative HPLC using acetonitrile/ammonium acetate buffer (50:50) as eluent (Example 43). After freeze drying the product, no crystalline material was identified.

It would be desirable to discover a form of elobixibat that is sufficiently robust to be suitable for formulation as a pharmaceutical.

During crystallization studies that form the basis for this invention, it was observed using X-ray powder diffraction (XRPD) techniques that elobixibat crystallized from many solvents or mixtures of solvents by incorporating solvent molecules in its structure, thereby forming specific solvates or mixed solvates. Thus, different crystal modifications of elobixibat were obtained in many solvents or combinations of solvents. Different crystal modifications were even obtained when the same solvent was used. Further, using thermal gravimetric analysis (TGA), it was concluded that different samples of the same crystal modification may contain different amounts of solvents. Additional crystal modifications of elobixibat were obtained when the incorporated organic solvent molecules were evaporated from the crystallized solvates. Thus, the experimental work supporting the present application found that many crystal modifications of elobixibat were unstable, and/or were observed to transform into other crystal modifications. It was therefore difficult to obtain consistent results by repeating similar experiments.

Different solvated crystal modifications may be revealed by using a very fast X-ray detector and withdrawing a wet sample from a slurry of the solid material to be analyzed onto a sample holder, keeping the sample at the experiment temperature and then analysing the sample quickly and repeatedly as it dries. This technique can show an initially formed solvate or mixed solvate, the desolvated modification or a mixture of the two. If more than one partially or completely desolvated crystal modification exists, there are even more possible variations of XRPD-data. It was thus a further challenge just to obtain XRPD-data for a pure crystal modification.

Various crystal modifications may have disadvantages including a variable degree of crystallinity and difficulties in handling and formulating. Thus, there is a need for stable crystal modifications of elobixibat having improved properties with respect to stability, bulk handling and solubility. It is therefore an object of the present invention to provide a stable and highly crystalline crystal modification of elobixibat.

SUMMARY OF THE INVENTION

The invention provides various crystal modifications of elobixibat. In one aspect, the crystal modification is a monohydrate of elobixibat. A monohydrate includes 0.9-1.1 moles of water associated with a crystal per mole of elobixibat. The amount of water calculated herein excludes water adsorbed to the surface of the crystal. In certain embodiments, the monohydrate is stable for at least one year, such as at least 17 months.

In another aspect, which may be related to the first aspect, the invention provides a crystalline monohydrate of elobixibat, where the crystalline form is prepared by forming an elobixibat monoalcoholate, substantially converting the monoalcoholate to an ansolvate and exposing the ansolvate to water vapor. The monoalcoholate can be a methanolate, an ethanolate, a 1-propanolate, a 2-propanolate or a mixture of these alcohols. In certain embodiments, the monohydrate cannot be formed without forming a monoalcoholate as an intermediate.

The invention also includes other crystal modifications including crystal modification I and crystal modification IV, along with intermediates used to prepare these crystal modifications.

The invention further provides methods of treating a condition described herein and use of the crystal modifications described herein in treating a condition described herein and in the manufacture of a medicament for the treatment of a condition described herein.

DETAILED DESCRIPTION OF THE INVENTION

In a first aspect, the invention relates to crystal modification IV of elobixibat. It has surprisingly been found that this very stable crystal modification of elobixibat can be obtained, starting from what was initially thought to be the most stable dried form, crystal modification I. Crystal modification I was used as the drug substance in Phase I and II clinical trials. When this crystal modification I is slurried in ethanol or a mixture of ethanol and water at a temperature between about 0 and 70° C., such as between about 0 and 25° C., another crystal modification is gradually obtained, namely the ethanol solvate EtOH-1. This solvate has been confirmed to be a monoethanolate. Upon drying this solvate, such as under reduced pressure and elevated temperature, EtOH-1 loses its solvate molecules and turns into a partly crystalline ansolvate. When the ansolvate is subsequently exposed to moisture from the air, it readily absorbs one equivalent of water. During these two phase transformations, the crystal structure is more or less preserved. The resulting monohydrate, hereinafter referred to as crystal modification IV, was found to be stable for at least up to 17 months of storage, such as under ambient, open conditions. This crystal modification furthermore has better thermodynamic stability and a higher, more consistent degree of crystallinity than crystal modification I and other, less crystalline forms of elobixibat.

Figure 6:
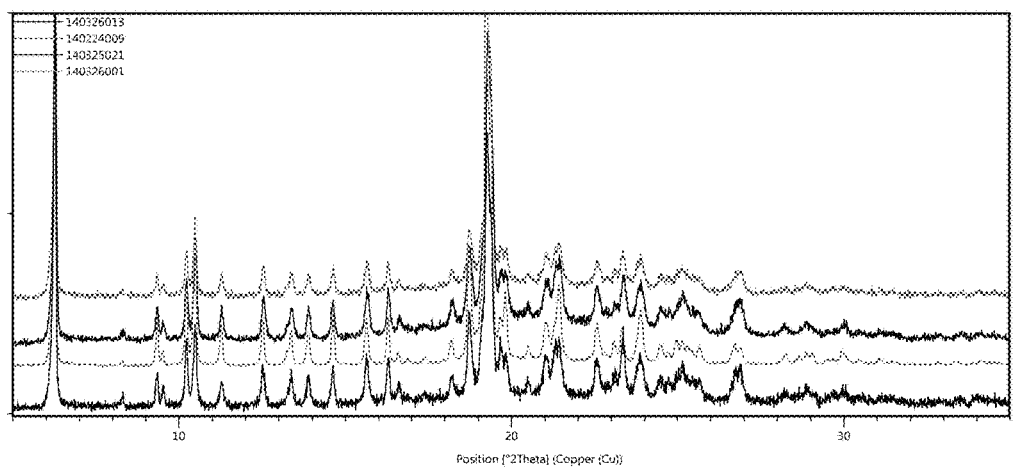
FIG. 6 shows the X-ray powder diffractogram of crystal modification IV obtained (from the bottom) from methanol, ethanol, 1-propanol and 2-propanol.

It was thereafter discovered that elobixibat behaves similarly in other alcohols, such as methanol, 1-propanol and 2-propanol, or a 50:50 volume mixture of alcohol and water at room temperature. Under these conditions, the solvates MeOH-1, 1-PrOH-1 and 2-PrOH-1, which are substantially isostructural with EtOH-1, may be obtained from a slurry. The alcohol solvates thus formed behave similarly to EtOH-1, in that they form an intermediate as they begin to lose their solvate molecules and then, when the alcohol has been substantially evaporated off, absorb water and transform to modification IV. FIG. 6 shows X-ray powder diffraction data for modification IV, obtained from different alcohols.

The isolation of this stable crystal modification IV was not straightforward. Although crystal modification IV is a monohydrate, it cannot be obtained directly from crude elobixibat or crystal modification I, because when these are stirred in a mixture of water and alcohol, the alcohol solvate (MeOH-1, EtOH-1, 1-PrOH-1 or 2-PrOH-1) is formed instead. The alcohol solvate is believed to be the thermodynamically more stable crystal modification under these conditions. Interestingly, the alcohol solvate does not spontaneously transform into crystal modification IV either—not even when exposed to 100% relative humidity—if the alcohol molecules are not first removed, for example by drying, from the crystal structure of the solvate.

In one embodiment, the invention relates to crystal modification IV having an X-ray powder diffraction (XRPD) pattern, obtained with CuKα1-radiation, with at least specific peaks at ° 2θ positions 6.3±0.2 and/or 19.4±0.2.

In another embodiment, the invention relates to crystal modification IV having an XRPD pattern, obtained with CuKα1-radiation, with specific peaks at ° 2θ positions 6.3±0.2 and 19.4±0.2 and one or more of the characteristic peaks: 10.2±0.2, 10.5±0.2, 9.4±0.2, 9.5±0.2, 12.5±0.2, 14.6±0.2, 15.6±0.2, and 23.3±0.2.

In another embodiment, the invention relates to crystal modification IV having an XRPD pattern, obtained with CuKα1-radiation, with specific peaks at ° 2θ positions 6.3±0.2, 19.4±0.2, 10.2±0.2, 10.5±0.2, 9.4±0.2, and 9.5±0.2.

In another embodiment, the invention relates to crystal modification IV having an XRPD pattern, obtained with CuKα1-radiation, with characteristic peaks at ° 2θ positions 6.3±0.2, 19.4±0.2, 10.2±0.2, 10.5±0.2, 9.4±0.2, 9.5±0.2, 12.5±0.2, 14.6±0.2, 15.6±0.2, 23.3±0.2, and one or more of 8.3±0.2, 11.3±0.2, 13.4±0.2, 13.9±0.2, 16.3±0.2, 16.6±0.2, 18.2±0.2, 18.8±0.2, 19.1±0.2, 19.3±0.2, 19.7±0.2, 19.8±0.2, 20.5±0.2, 21.0±0.2, 21.3±0.2, 21.4±0.2, 22.6±0.2, 22.9 0.2, 23.1±0.2, 23.9±0.2, 24.5±0.2, 24.7±0.2, 25.0±0.2, 25.2±0.2, 25.4±0.2, 25.7±0.2, 26.7±0.2, 26.9±0.2, 28.3±0.2, and 28.9±0.2.

According to one embodiment the invention relates to crystal modification IV having an XRPD pattern, obtained with CuKα1-radiation, with characteristic peaks at ° 2θ positions: 6.3±0.2, 8.3±0.2, 9.4±0.2, 9.5±0.2, 10.2±0.2, 10.5±0.2, 11.3±0.2, 12.5±0.2, 13.4±0.2, 13.9±0.2, 14.6±0.2, 15.6±0.2, 16.3±0.2, 16.6±0.2, 18.2±0.2, 18.8±0.2, 19.1±0.2, 19.3±0.2, 19.4±0.2, 19.7±0.2, 19.8±0.2, 20.5±0.2, 21.0±0.2, 21.3±0.2, 21.4±0.2, 22.6±0.2, 22.9±0.2, 23.1±0.2, 23.3±0.2, 23.9±0.2, 24.5±0.2, 24.7±0.2, 25.0±0.2, 25.2±0.2, 25.4±0.2, 25.7±0.2, 26.7±0.2, 26.9±0.2, 28.3±0.2, and 28.9±0.2.

Figure 1:
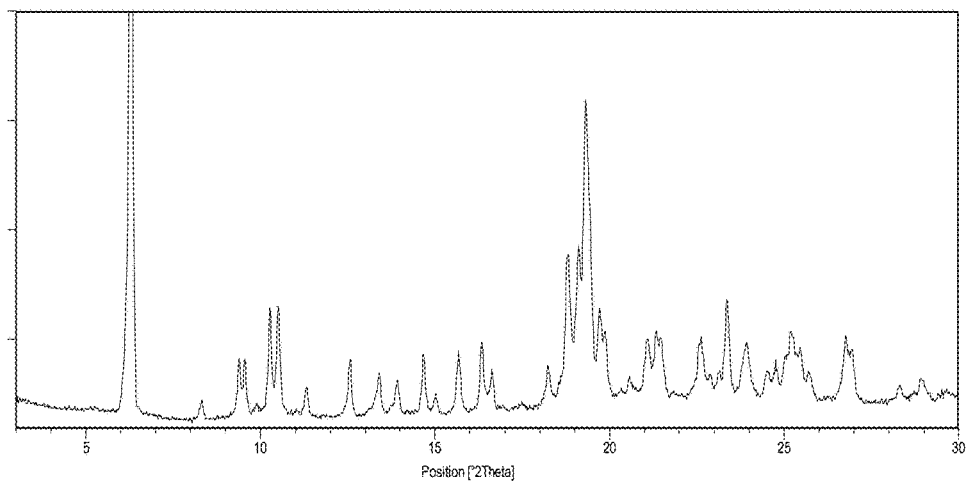
FIG. 1 shows the X-ray powder diffractogram of crystal modification IV.

In yet another embodiment, the invention relates to crystal modification IV having an XRPD pattern, obtained with CuKα1-radiation, substantially as shown in FIG. 1.

In a second aspect, the invention relates to crystal modification EtOH-1 of elobixibat.

In one embodiment, the invention relates to crystal modification EtOH-1 having an XRPD pattern, obtained with CuKα1-radiation, with characteristic peaks at ° 2θ positions 6.1±0.2 and 18.9±0.2 or having characteristic peaks at ° 2θ positions 6.1±0.2 and 18.9±0.2 and one or more of the characteristic peaks: 10.1±0.2, 14.5±0.2, 18.4±0.2, 19.1±0.2, 20.7±0.2, 10.4±0.2, 13.1±0.2, and 11.1±0.2.

In another embodiment, the invention relates to crystal modification EtOH-1 having an XRPD pattern, obtained with CuKα1-radiation, with characteristic peaks at ° 2θ positions: 6.1±0.2, 18.9±0.2, 10.1±0.2, 14.5±0.2, 18.4±0.2, 19.1±0.2, 20.7±0.2, 10.4±0.2, 13.1±0.2, 11.1±0.2 and one or more of 8.0±0.2, 9.3±0.2, 12.2±0.2, 13.7±0.2, 15.1±0.2, 15.3±0.2, 15.9±0.2, 17.2±0.2, 17.8±0.2, 20.3±0.2, 21.2±0.2, 22.0±0.2, 22.2±0.2, 22.5±0.2, 23.6±0.2, 24.0±0.2, 24.5±0.2, 24.7±0.2, 25.2±0.2, and 26.3±0.2.

In another embodiment, the invention relates to crystal modification EtOH-1 having an XRPD pattern, obtained with CuKα1-radiation, with characteristic peaks at ° 2θ positions: 6.1±0.2, 8.0±0.2, 9.3±0.2, 10.1±0.2, 10.4±0.2, 11.1±0.2, 12.2±0.2, 13.1±0.2, 13.7±0.2, 14.5±0.2, 15.1±0.2, 15.3±0.2, 15.9±0.2, 17.2±0.2, 17.8±0.2, 18.4±0.2, 18.9±0.2, 19.1±0.2, 20.3±0.2, 20.7±0.2, 21.2±0.2, 22.0±0.2, 22.2±0.2, 22.5±0.2, 23.6±0.2, 24.0±0.2, 24.5±0.2, 24.7±0.2, 25.2±0.2, and 26.3±0.2.

Figure 2:
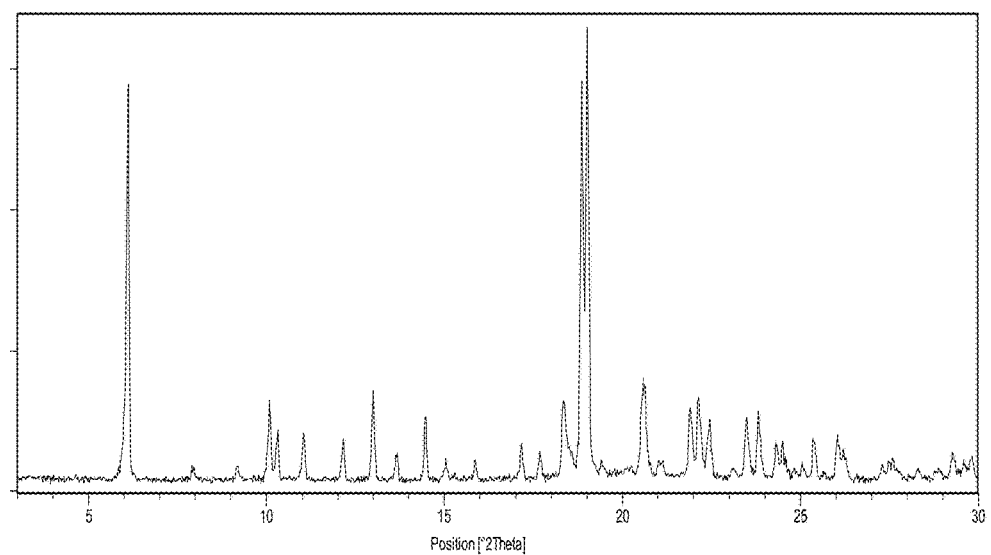
FIG. 2 shows the X-ray powder diffractogram of crystal modification EtOH-1.

In yet another embodiment, the invention relates to crystal modification EtOH-1 having an XRPD pattern, obtained with CuKα1-radiation, substantially as shown in FIG. 2.

In a third aspect, the invention relates to crystal modification MeOH-1 of elobixibat.

In one embodiment, the invention relates to crystal modification MeOH-1 having an XRPD pattern, obtained with CuKα1-radiation, with characteristic peaks at ° 2θ positions 6.2±0.2 and 18.9±0.2 or having characteristic peaks at ° 2θ positions 6.2±0.2 and 18.9±0.2 and one or more of the characteristic peaks: 10.1±0.2, 14.6±0.2, 18.6±0.2, 19.1±0.2, 22.2±0.2, 24.7±0.2, 12.3±0.2, 13.3±0.2, and 16.1±0.2.

In another embodiment, the invention relates to crystal modification MeOH-1 having an XRPD pattern, obtained with CuKα1-radiation, with characteristic peaks at ° 2θ positions: 6.2±0.2, 18.9±0.2, 10.1±0.2, 14.6±0.2, 18.6±0.2, 19.1±0.2, 22.2±0.2, 24.7±0.2, 12.3±0.2, 13.3±0.2, 16.1±0.2 and one or more of 8.1±0.2, 9.3±0.2, 10.5±0.2, 10.9±0.2, 13.0±0.2, 14.4±0.2, 15.8±0.2, 17.6±0.2, 20.3±0.2, 20.7±0.2, 21.0±0.2, 22.7±0.2, 24.0±0.2, 24.3±0.2 and 26.1±0.2.

In another embodiment, the invention relates to crystal modification MeOH-1 having an XRPD pattern, obtained with CuKα1-radiation, with characteristic peaks at ° 2θ positions: 6.2±0.2, 8.1±0.2, 9.3±0.2, 10.1±0.2, 10.5±0.2, 10.9±0.2, 12.3±0.2, 13.0±0.2, 13.3±0.2, 14.4±0.2, 14.6±0.2, 15.8±0.2, 16.1±0.2, 17.6±0.2, 18.6±0.2, 18.9±0.2, 19.1±0.2, 20.3±0.2, 20.7±0.2, 21.0±0.2, 22.2±0.2, 22.7±0.2, 24.0±0.2, 24.3±0.2, 24.7±0.2, and 26.1±0.2.

Figure 8:
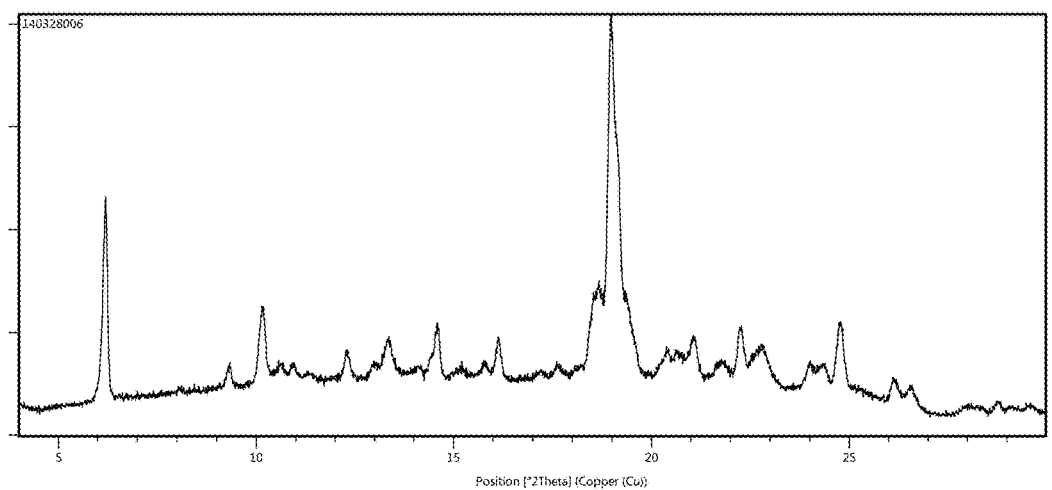
FIG. 8 shows the X-ray powder diffractogram of crystal modification MeOH-1.

In yet another embodiment, the invention relates to crystal modification MeOH-1 having an XRPD pattern, obtained with CuKα1-radiation, substantially as shown in FIG. 8.

In a fourth aspect, the invention relates to crystal modification 1-PrOH-1 of elobixibat.

In one embodiment, the invention relates to crystal modification 1-PrOH-1 having an XRPD pattern, obtained with CuKα1-radiation, with characteristic peaks at ° 2θ positions 6.1±0.2 and 19.0±0.2 or having characteristic peaks at ° 2θ positions 6.1±0.2 and 19.0±0.2 and one or more of the characteristic peaks: 10.0±0.2, 14.4±0.2, 18.3±0.2, 18.8±0.2, 20.5±0.2, 10.3±0.2, 13.0±0.2, and 11.0±0.2.

In another embodiment, the invention relates to crystal modification 1-PrOH-1 having an XRPD pattern, obtained with CuKα1-radiation, with characteristic peaks at ° 2θ positions: 6.1±0.2, 19.0±0.2, 10.0±0.2, 14.4±0.2, 18.3±0.2, 18.8±0.2, 20.5±0.2, 10.3±0.2, 13.0±0.2, 11.0±0.2 and one or more of 7.9±0.2, 9.2±0.2, 12.1±0.2, 13.6±0.2, 15.0±0.2, 15.3±0.2, 15.8±0.2, 17.1±0.2, 17.6±0.2, 20.2±0.2, 21.1±0.2, 21.9±0.2, 22.1±0.2, 22.4±0.2, 23.5±0.2, 23.8±0.2, 24.3±0.2, 24.5±0.2, 25.4±0.2, and 26.2±0.2.

In another embodiment, the invention relates to crystal modification 1-PrOH-1 having an XRPD pattern, obtained with CuKα1-radiation, with characteristic peaks at ° 2θ positions: 6.1±0.2, 7.9±0.2, 9.2±0.2, 10.0±0.2, 10.3±0.2, 11.0±0.2, 12.1±0.2, 13.0±0.2, 13.6±0.2, 14.4±0.2, 15.0±0.2, 15.3±0.2, 15.8±0.2, 17.1±0.2, 17.6±0.2, 18.3±0.2, 18.5±0.2, 18.8±0.2, 19.0±0.2, 19.4±0.2, 20.2±0.2, 20.5±0.2, 21.1±0.2, 21.9±0.2, 22.1±0.2, 22.4±0.2, 23.1±0.2, 23.5±0.2, 23.8±0.2, 24.3±0.2, 24.5±0.2, 25.4±0.2, 26.0±0.2 and 26.2±0.2.

Figure 9:
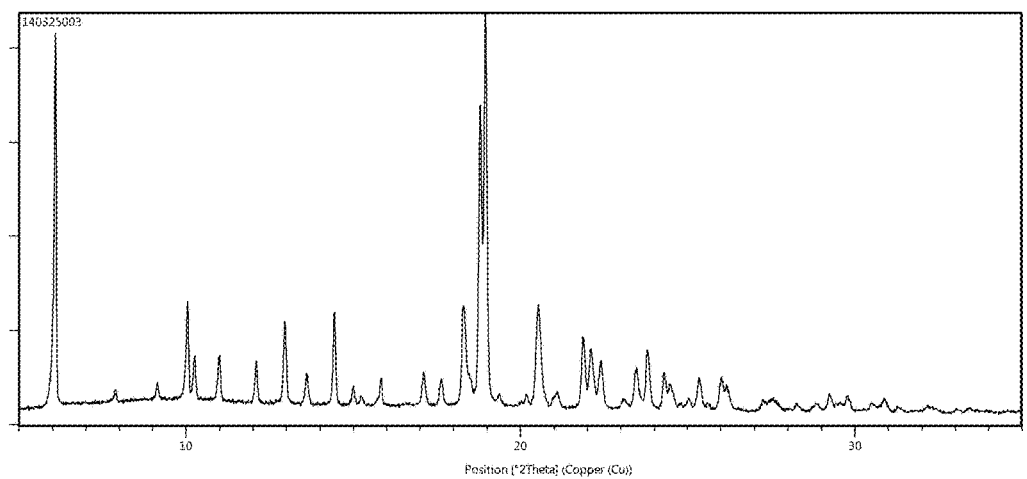
FIG. 9 shows the X-ray powder diffractogram of crystal modification 1-PrOH-1.

In yet another embodiment, the invention relates to crystal modification 1-PrOH-1 having an XRPD pattern, obtained with CuKα1-radiation, substantially as shown in FIG. 9.

In a fifth aspect, the invention relates to crystal modification 2-PrOH-1 of elobixibat.

In one embodiment, the invention relates to crystal modification 2-PrOH-1 having an XRPD pattern, obtained with CuKα1-radiation, with characteristic peaks at ° 2θ positions 6.1±0.2 and 19.0±0.2 or having characteristic peaks at ° 2θ positions 6.1±0.2 and 19.0±0.2 and one or more of the characteristic peaks: 10.0±0.2, 14.4±0.2, 18.3±0.2, 18.8±0.2, 20.5±0.2, 10.3±0.2, 12.9±0.2, and 11.0±0.2.

In another embodiment, the invention relates to crystal modification 2-PrOH-1 having an XRPD pattern, obtained with CuKα1-radiation, with characteristic peaks at ° 2θ positions: 6.1±0.2, 19.0±0.2, 10.0±0.2, 14.4±0.2, 18.3±0.2, 18.8±0.2, 20.5±0.2, 10.3±0.2, 12.9±0.2, 11.0±0.2 and one or more of 9.1±0.2, 12.1±0.2, 13.6±0.2, 14.9±0.2, 15.2±0.2, 15.7±0.2, 17.1±0.2, 17.6±0.2, 18.5±0.2, 19.4±0.2, 20.2±0.2, 21.1±0.2, 21.7±0.2, 22.1±0.2, 22.3±0.2, 23.1±0.2, 23.4±0.2, 23.7±0.2, 24.1±0.2, 24.4±0.2, 24.6±0.2, 25.1±0.2, 25.4±0.2, 25.9±0.2, 26.2±0.2, 27.4±0.2 and 29.2±0.2.

In another embodiment, the invention relates to crystal modification 2-PrOH-1 having an XRPD pattern, obtained with CuKα1-radiation, with characteristic peaks at ° 2θ positions: 6.1±0.2, 9.1±0.2, 10.0±0.2, 10.3±0.2, 11.0±0.2, 12.1±0.2, 12.9±0.2, 13.6±0.2, 14.4±0.2, 14.9±0.2, 15.2±0.2, 15.7±0.2, 17.1±0.2, 17.6±0.2, 18.2±0.2, 18.5±0.2, 18.9±0.2, 19.0±0.2, 19.4±0.2, 20.2±0.2, 20.5±0.2, 21.1±0.2, 21.7±0.2, 22.1±0.2, 22.3±0.2, 23.1±0.2, 23.4±0.2, 23.7±0.2, 24.1±0.2, 24.4±0.2, 24.6±0.2, 25.0±0.2, 25.4±0.2, 25.9±0.2, 26.2±0.2, 27.4±0.2 and 29.2±0.2.

Figure 10:
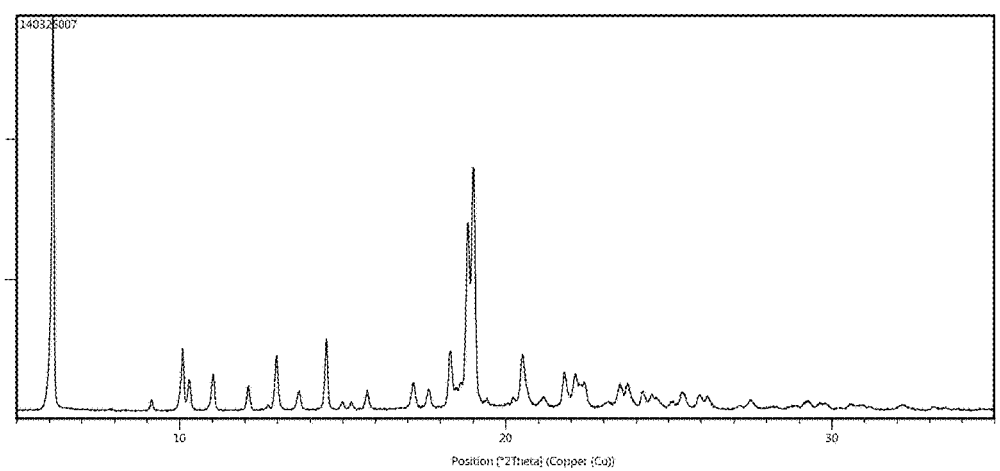
FIG. 10 shows the X-ray powder diffractogram of crystal modification 2-PrOH-1.

In yet another embodiment, the invention relates to crystal modification 2-PrOH-1 having an XRPD pattern, obtained with CuKα1-radiation, substantially as shown in FIG. 10.

In a sixth aspect, the invention relates to crystal modification I of elobixibat.

In one embodiment, the invention relates to crystal modification I having an XRPD pattern, obtained with CuKα1-radiation, with characteristic peaks at ° 2θ positions 5.2±0.2 and/or 10.0±0.2.

In another embodiment, the invention relates to crystal modification I having an XRPD pattern, obtained with CuKα1-radiation, with characteristic peaks at ° 2θ positions: 5.2±0.2 and 10.0±0.2 and one or more of the characteristic peaks: 4.9±0.2, 6.0±0.2, 7.6±0.2, 10.5±0.2, 11.3±0.2, 18.8±0.2, 20.4±0.2, and 22.9±0.2.

In another embodiment, the invention relates to crystal modification I having an XRPD pattern, obtained with CuKα1-radiation, with characteristic peaks at ° 2θ positions: 5.2±0.2, 10.0±0.2, 4.9±0.2, 6.0±0.2, 7.6±0.2, 10.5±0.2 and 11.3±0.2.

In another embodiment, the invention relates to crystal modification I having an XRPD pattern, obtained with CuKα1-radiation, with characteristic peaks at ° 2θ positions: 5.2±0.2, 10.0±0.2, 4.9±0.2, 6.0±0.2, 7.6±0.2, 10.5±0.2, 11.3±0.2, 18.8±0.2, 20.4±0.2, 22.9±0.2, and one or more of 3.1±0.2, 4.4±0.2, 7.4±0.2, 7.8±0.2, 8.2±0.2, 12.4±0.2, 13.3±0.2, 13.5±0.2, 14.6±0.2, 14.9±0.2, 16.0±0.2, 16.6±0.2, 16.9±0.2, 17.2±0.2, 17.7±0.2, 18.0±0.2, 18.3±0.2, 19.2±0.2, 19.4±0.2, 20.1±0.2, 20.7±0.2, 20.9±0.2, 21.1±0.2, 21.4±0.2, 21.8±0.2, 22.0±0.2, 22.3±0.2, 23.4±0.2, 24.0±0.2, 24.5±0.2, 24.8±0.2, 26.4±0.2, '27.1±0.2 and 27.8±0.2.

In another embodiment, the invention relates to crystal modification I having an XRPD pattern, obtained with CuKα1-radiation, with characteristic peaks at ° 2θ positions: 3,1±0.2, 4.4±0.2, 4.9±0.2, 5.2±0.2, 6.0±0.2, 7.4±0.2, 7.6±0.2, 7.8±0.2, 8.2±0.2, 10.0±0.2, 10.5±0.2, 11.3±0.2, 12.4±0.2, 13.3±0.2, 13.5±0.2, 14.6±0.2, 14.9±0.2, 16.0±0.2, 16.6±0.2, 16.9±0.2, 17.2±0.2, 17.7±0.2, 18.0±0.2, 18.3±0.2, 18.8±0.2, 19.2±0.2, 19.4±0.2, 20.1±0.2, 20.4±0.2, 20.7±0.2, 20.9±0.2, 21.1±0.2, 21.4±0.2, 21.8±0.2, 22.0±0.2, 22.3±0.2, 22.9±0.2, 23.4±0.2, 24.0±0.2, 24.5±0.2, 24.8±0.2, 26.4±0.2. '27.1±0.2 and 27.8±0.2.

Figure 4:
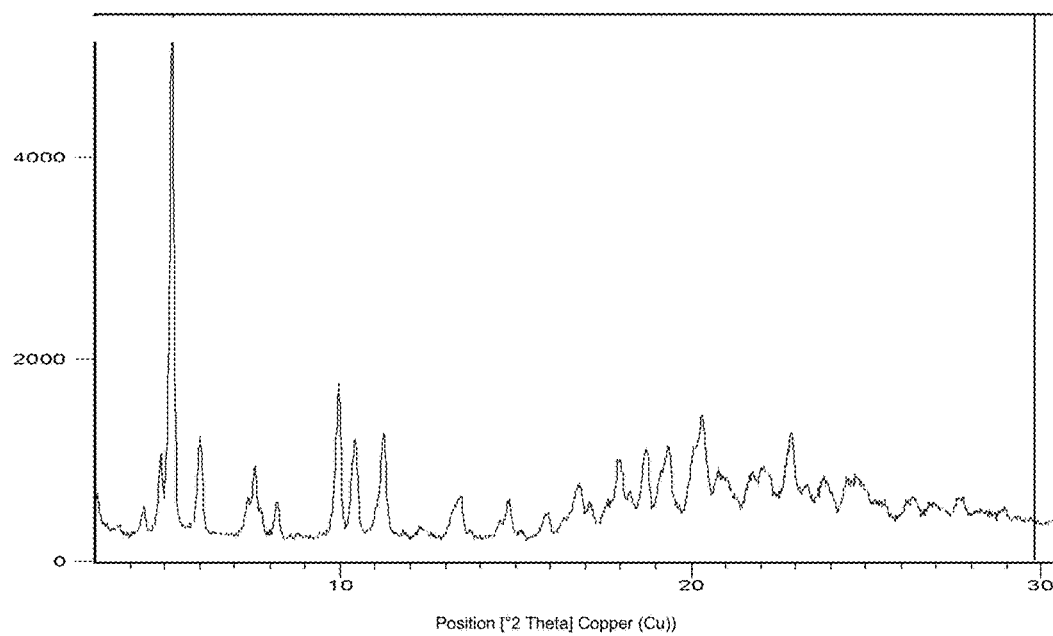
FIG. 4 shows the X-ray powder diffractogram of crystal modification I.

In yet another embodiment, the invention relates to crystal modification I having an XRPD pattern, obtained with CuKα1-radiation, substantially as shown in FIG. 4.

An advantage with crystal modification IV is that it is more thermodynamically stable at normal conditions (21° C., 10-30% relative humidity) than crystal modification I and other crystal modifications of elobixibat obtained from methanol, ethanol, 1-propanol or 2-propanol, or from mixtures of any of these alcohols and water. This allows for a stable and secure manufacturing process of the drug substance and drug formulation.

Certain forms of elobixibat, such as crystal modification I of elobixibat, contain a non-stoichiometric amount of water. In such forms, the amount of water may vary (e.g., dependent on the relative humidity of the air, or between different batches). In contrast, crystal modification IV is a stoichiometric monohydrate, i.e. it contains about one mole of water per mole of substance (typically from 0.9-1.1 moles of water per mole of substance, not including water adsorbed to the surface of a crystal). This gives crystal modification IV a more stable weight at varying relative humidity.

Crystal modification IV is a highly crystalline monohydrate, which can be produced by a controlled transformation process via the ethanol solvate EtOH-1 or via the isostructural alcohol solvates MeOH-1, 1-PrOH-1 and 2-PrOH-1. The crystal structure of EtOH-1 remains similar when the ethanol is evaporated and replaced by water. Further, the relatively stable degree of crystallinity of crystal modification IV results in a reproducible solubility of the compound. This is of special importance for compounds that are to be used in pharmaceutical preparations, where each tablet or capsule containing the active pharmaceutical ingredient should have the same pharmacological properties. Thus, crystal modification IV is more favourable for preparing pharmaceutical formulations of elobixibat than other crystal modifications of elobixibat discovered to date.

Yet another advantage with crystal modification IV is that the crystal habit is more three dimensional compared to the crystal modification I, which is more two dimensional (needle shaped). This gives crystal modification IV advantageous properties with regard to bulk handling and formulation. For instance, there is reduced or even no need to sieve the material, for example to break such crystals, and it can more easily be mixed with excipients during formulation.

In another aspect, the invention relates to a process for the preparation of crystal modification IV. This process involves the preparation and isolation of crystal modification EtOH-1, or one of the isostructural alcohol solvates MeOH-1, 1-PrOH-1 and 2-PrOH-1, from either crude or pure elobixibat. In one embodiment, the process comprises the steps of:

a) preparing a saturated solution of elobixibat in alcohol or a mixture of alcohol and water in a vessel;

b) adding an excess of elobixibat to the saturated solution of step a) so as to obtain a slurry;

c) maintaining stirring of the slurry, optionally at about 5 to 25° C., preferably 20 to 25° C. for a period of several hours up to several days or even a week or more;

d) recovering the solid obtained in step c), followed by drying the solid in vacuum until removal of substantially all alcohol; and e) exposing the dry solid obtained in step d) to moisture from the air.

The crude or pure starting material in step a) is amorphous elobixibat or another crystal modification of elobixibat. In certain embodiments, elobixibat is essentially free from solvents other than water. In a preferred embodiment, the starting material is crystal modification I, which is a relatively stable crystal modification of elobixibat. Crystal modification I can be obtained from crude, amorphous elobixibat, as described in the experimental section. Its X-ray powder diffractogram is showed in FIG. 4.

In certain embodiments, the saturated solution of elobixibat used in step a) is free from any solvents except methanol, ethanol, 1-propanol, 2-propanol and water, such as less than 0.5% w/w solvents except methanol, ethanol, 1-propanol, 2-propanol and water. If a mixture of methanol and water, ethanol and water, 1-propanol and water or 2-propanol and water is used, the amount of methanol, ethanol, 1-propanol or 2-propanol should be at least 5% w/w in certain embodiments. Most preferably, the solvent is at least 90% or even 100% w/w methanol, ethanol, 1-propanol or 2-propanol.

The solid obtained in step c) is crystal modification MeOH-1, EtOH-1, 1-PrOH-1 or 2-PrOH-1. It is believed that in methanol, ethanol, 1-propanol or 2-propanol, or in a mixture of methanol, ethanol, 1-propanol or 2-propanol and water, crystal modification MeOH-1, EtOH-1, 1-PrOH-1 or 2-PrOH-1 is the most thermodynamically stable form. Thus, when the suspension of step b) is stirred at about 5 to 25° C., such as 20-25° C. (preferably for methanol), for a longer period of time, at such temperature, MeOH-1, EtOH-1, 1-PrOH-1 or 2-PrOH-1 will crystallize.

Crystal modification MeOH-1 is a methanol solvate, crystal modification EtOH-1 is an ethanol solvate, crystal modification 1-PrOH-1 is a 1-propanol solvate and crystal modification 2-PrOH-1 is a 2-propanol solvate. When these solvates are dried under reduced pressure and elevated temperature, they lose their alcohol molecules and turn into an ansolvate. In order to obtain a full transformation from the alcohol solvate form to the monohydrate form, MeOH-1, EtOH-1, 1-PrOH-1 or 2-PrOH-1 must be dried, so as to substantially remove the alcohol embedded in the crystals. Preferably, the solid is dried under vacuum at elevated temperatures, such as about 50° C., or such as about 65° C.

When the ansolvate crystals are exposed to moisture from the air, water molecules are absorbed and a monohydrate is formed, crystal modification IV. Absorption of water takes place at relative humidity as low as 10%. For reproducible results and high degree of crystallinity, it is preferred that the anhydrate crystals are exposed to air at a relative humidity of 20-60% at 25° C. By means of thermal gravimetric analysis, differential scanning calorimetry, Karl Fischer titration and Dynamic Vapor Sorption analysis, it has been shown that crystal modification IV is a monohydrate.

Alternatively, crystal modification IV can be prepared by adding seed crystals to a saturated solution of elobixibat in methanol, ethanol, 1-propanol or 2-propanol or a mixture of methanol, ethanol, 1-propanol or 2-propanol and water. Thus, in another embodiment, the process comprises the steps of:
 a) preparing an supersaturated solution of elobixibat in alcohol or a mixture of alcohol and water, in a vessel;
 b) adding seed crystals to the supersaturated solution of step a);
 c) maintaining stirring until a solid is obtained;
 d) recovering the solid obtained in step c), followed by drying the solid in vacuum until removal of the alcohol; and
 e) exposing the dry solid obtained in step d) to moisture from the air.

The crude or pure starting material in step a) is amorphous elobixibat or another crystal modification of elobixibat which in certain embodiments is free from solvents other than alcohol and water.

In certain embodiments, the supersaturated solution of elobixibat used in step a) is free from any solvents except alcohol and water, such as less than 0.5% solvents except alcohol and water. If a mixture of alcohol and water is used, the amount of alcohol should be at least 5% w/w in certain embodiments. Preferably, the solvent is methanol, ethanol, 1-propanol or 2-propanol.

The supersaturated solution can be prepared by dissolving starting material in warm methanol, ethanol, 1-propanol or 2-propanol or a warm mixture of methanol, ethanol, 1-propanol or 2-propanol and water, and then cooling the resulting solution. The warm solvent preferably has an initial temperature of about 40 to 45° C., and the solution is then cooled to a temperature such as about 25° C.

The seed crystals should be of crystal modification IV. The addition of seed crystals will accelerate the formation and crystallization of MeOH-1, EtOH-1, 1-PrOH-1 or 2-PrOH-1. The stirring time in step c) can therefore be considerably shorter, such as 15 hours, or such as 10 hours. The stirring can be maintained at a lower temperature, such as 5 to 10° C., or such as 0 to 5° C.

Interestingly, even though crystal modification IV is a monohydrate, it cannot be obtained directly from crystal modification I when stirred in a mixture of water and methanol, ethanol, 1-propanol or 2-propanol. In such a mixture, crystal modification I transforms into the alcohol solvate MeOH-1, EtOH-1, 1-PrOH-1 or 2-PrOH-1, respectively, all of which are believed to be a thermodynamically more stable crystal modification than crystal modification I under these conditions. Surprisingly, when the formed MeOH-1, EtOH-1, 1-PrOH-1 or 2-PrOH-1 subsequently is exposed to 100% relative humidity, it still does not transform into the monohydrate. This shows that the alcohol molecules must be substantially removed from the crystal structure before water molecules can enter and change the structure to crystal modification IV.

Figure 3:
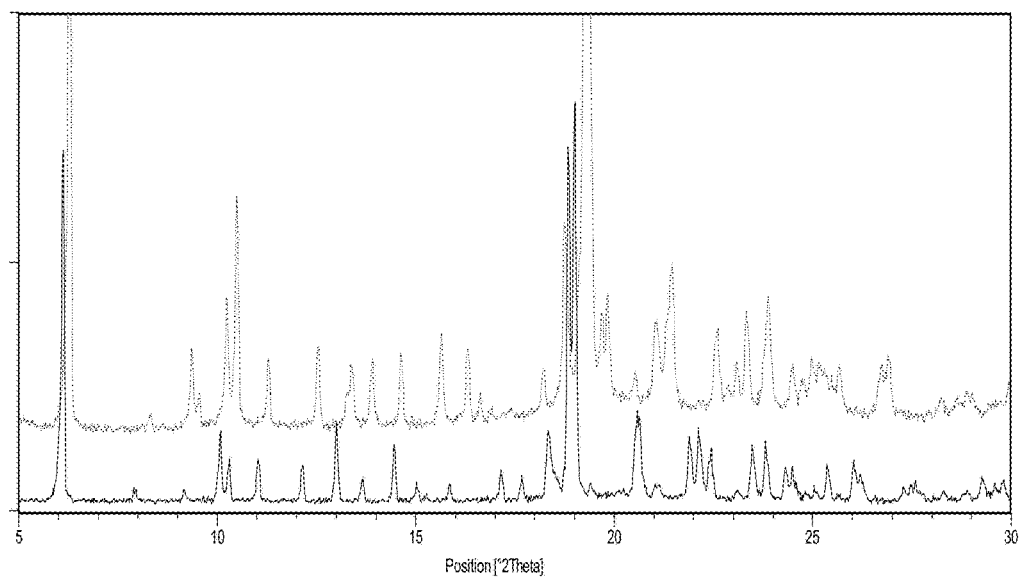
FIG. 3 shows a comparison between the X-ray powder diffractograms for crystal modifications EtOH-1 (solid line, bottom) and IV (dotted line, top).
Figure 7:
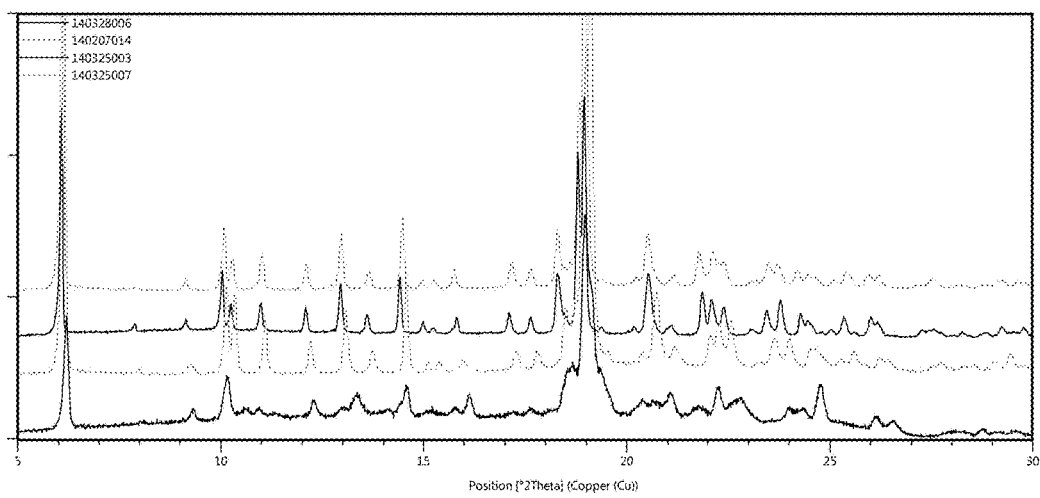
FIG. 7 shows the X-ray powder diffractogram of crystal modifications (from the bottom) MeOH-1, EtOH-1, 1-PrOH-1 and 2-PrOH-1 obtained from methanol, ethanol, 1-propanol and 2-propanol.

When crystal modification IV is stirred in methanol, ethanol, 1-propanol or 2-propanol, or in a mixture of methanol, ethanol, 1-propanol or 2-propanol and water, it transforms again into MeOH-1, EtOH-1, 1-PrOH-1 or 2-PrOH-1. It is speculated that this transformation occurs within only a few minutes. This is likely a result of the high degree of similarity between the XRPD patterns for crystal modifications MeOH-1, EtOH-1, 1-PrOH-1, 2-PrOH-1 and IV (see FIG. 3 and FIG. 7). Since the patterns are so similar, it is believed, albeit without reliance on such theory, that the transformation may occur without dissolution and subsequent re-crystallization, but rather by a rearrangement in the solid state.

Elobixibat is an ileal bile acid transporter (IBAT) inhibitor. The ileal bile acid transporter (IBAT) is the main mechanism for re-absorption of bile acids from the GI tract. Partial or full blockade of that IBAT mechanism will result in lower concentration of bile acids in the small bowel wall, portal vein, liver parenchyma, intrahepatic biliary tree, and extrahepatic biliary tree, including the gall bladder. Diseases which may benefit from partial or full blockade of the IBAT mechanism may be those having, as a primary pathophysiological defect, symptoms of excessive concentration of bile acids in serum and in the above organs.

Thus, in another aspect, the invention also relates to crystal modification IV of elobixibat for use in therapy.

Crystal modification IV is useful in the prophylaxis or treatment of hypercholesterolemia, dyslipidemia, metabolic syndrome, obesity, disorders of fatty acid metabolism, glucose utilization disorders, disorders in which insulin resistance is involved, type 1 and type 2 diabetes mellitus, liver diseases, diarrhoea during therapy comprising an IBAT inhibitor compound, constipation including chronic constipation, e.g. functional constipation, including chronic constipation and constipation predominant irritable bowel syndrome (IBS-C). Treatment and prophylaxis of constipation is described in WO 2004/089350.

Further potential diseases to be treated with the crystal modification IV are selected from the group consisting of liver parenchyma, inherited metabolic disorders of the liver, Byler syndrome, primary defects of bile acid (BA) synthesis such as cerebrotendinous xanthomatosis, secondary defects such as Zellweger's syndrome, neonatal hepatitis, cystic fibrosis (manifestations in the liver), ALGS (Alagilles syndrome), progressive familial intrahepatic cholestasis (PFIC), autoimmune hepatitis, primary biliary cirrhosis (PBC), liver fibrosis, non-alcoholic fatty liver disease, NAFLD/NASH, portal hypertension, general cholestasis such as in jaundice due to drugs or during pregnancy, intra- and extrahepatic cholestasis such as hereditary forms of cholestasis such as PFIC1, primary sclerosing cholangitis (PSC), gall stones and choledocholithiasis, malignancy causing obstruction of the biliary tree, symptoms (scratching, pruritus) due to cholestasis/jaundice, pancreatitis, chronic autoimmune liver disease leading to progressive cholestasis, pruritus of cholestatic liver disease and disease states associated with hyperlipidaemic conditions.

Other diseases to be treated with the crystal modification IV are selected from the group consisting of hepatic disorders and conditions related thereto, fatty liver, hepatic steatosis, non-alcoholic steatohepatitis (NASH), alcoholic hepatitis, acute fatty liver, fatty liver of pregnancy, drug-induced hepatitis, iron overload disorders, hepatic fibrosis, hepatic cirrhosis, hepatoma, viral hepatitis and problems in relation to tumours and neoplasmas of the liver, of the biliary tract and of the pancreas.

Thus, in one embodiment, the invention relates to crystal modification IV of elobixibat for use in the treatment and/or prophylaxis of a disease or disorder as listed above.

In another embodiment, the invention relates to the use of crystal modification IV of elobixibat in the manufacture of a medicament for the treatment and/or prophylaxis of a disease or disorder as listed above.

In yet another embodiment, the invention relates to a method of treatment and/or prophylaxis of a disease or disorder as listed above in a warm-blooded animal, comprising administering an affective amount of crystal modification IV of elobixibat to a warm-blooded animal in need of such treatment and/or prophylaxis.

Another aspect of the invention relates to a pharmaceutical composition comprising an effective amount of crystal modification IV, in association with a pharmaceutically acceptable diluent or carrier.

Yet another aspect of the invention relates to the use of crystal modification IV in the preparation of a pharmaceutical composition, comprising admixing crystal modification IV with a pharmaceutically acceptable diluent or carrier.

The pharmaceutical composition may further comprise at least one other active substance, such as an active substance selected from an IBAT inhibitor; an enteroendocrine peptide or enhancer thereof; a dipeptidyl peptidase-IV inhibitor; a biguanidine; an incretin mimetic; a thiazolidinone; a PPAR agonist; a HMG Co-A reductase inhibitor; a bile acid binder; a TGR5 receptor modulator; a member of the prostone class of compounds; a guanylate cyclase C agonist; a 5-HT4 serotonin agonist; or a pharmaceutically acceptable salt of any one these active substances. Examples of such combinations are also described in WO2012/064268.

Crystal modification IV will normally be administered to a warm-blooded animal at a unit dose within the range of 5 to 5000 mg per square meter body area, i.e. approximately 0.1 to 100 mg/kg or 0.01 to 50 mg/kg, and this normally provides a therapeutically-effective dose. A unit dose form, such as a tablet or capsule, will usually contain about 1 to 250 mg of active ingredient, such as about 1 to 100 mg, or about 5 to 50 mg, e.g. about 1 to 20 mg. The daily dose can be administered as a single dose or divided into one, two, three or more unit doses.

An orally administered daily dose of an IBAT inhibitor is preferably within 0.1 to 1000 mg, more preferably 1 to 100 mg, such as 5 to 15 mg.

The dosage required for the therapeutic or prophylactic treatment will depend on the route of administration, the severity of the disease, the age and weight of the patient and other factors normally considered by the attending physician when determining the individual regimen and dosage levels appropriate for a particular patient.

Definitions

The term "crystal modification" refers to a crystalline solid phase of an organic compound. A crystal modification can be either a solvate or an ansolvate.

The term "solvate" refers to a crystalline solid phase of an organic compound, which has solvent molecules incorporated into its crystal structure. A "hydrate" is a solvate wherein the solvent is water, whereas a "mixed solvate" is a solvate containing molecules from more than one solvent.

The term "slurry" refers to a saturated solution to which an overshoot of solid is added, thereby forming a mixture of solid and saturated solution, a "slurry".

As used herein, the terms "treatment," "treat," and "treating" refer to reversing, alleviating, delaying the onset of, or inhibiting the progress of a disease or disorder, or one or more symptoms thereof, as described herein. In some embodiments, treatment may be administered after one or more symptoms have developed. In other embodiments, treatment may be administered in the absence of symptoms. For example, treatment may be administered to a susceptible individual prior to the onset of symptoms (e.g., in light of a history of symptoms and/or in light of genetic or other susceptibility factors). Treatment may also be continued after symptoms have resolved, for example to prevent or delay their recurrence.

When reference is made herein to a crystalline compound, preferably the crystallinity as estimated by X-ray powder diffraction data is greater than about 70%, such as greater than about 80%, particularly greater than about 90%, more particularly greater than about 95%. In embodiments of the invention, the degree of crystallinity as estimated by X-ray powder diffraction data is greater than about 98%, preferably greater than about 99%, wherein the % crystallinity refers to the percentage by weight of the total sample mass which is crystalline.

Preferably a crystal modification according to the invention is substantially free from other crystal modifications of the compound. Preferably, the described crystal modifications of elobixibat includes less than, for example, 20%, 15%, 10%, 5%, 3%, or particularly, less than 1% by weight of other crystal modifications of elobixibat. Thus, preferably, the purity of the described crystal modifications of elobixibat is >80%, >85%, >90%, >95%, >97%, or particularly >99%.

The invention will now be described by the following examples which do not limit the invention in any respect. All cited documents and references are incorporated by reference.

Abbreviations
cr. mod. crystal modification
EtOH ethanol
h hour(s)
HDPE high density polyethylene
LDPE low density polyethylene
MeOH methanol
min. minute(s)
1-PrOH 1-propanol
2-PrOH 2-propanol

EXPERIMENTAL METHODS

X-Ray Powder Diffraction (XRPD) Analysis

Dry samples were lightly ground in an agate mortar, if needed, and were then smeared out on a sample holder. Slurry samples were added to the sample holder as wet and were analyzed both wet and dry. XRPD data were collected on a cut Silicon Zero Background Holder (ZBH) or on a Porous Alumina Filter Sample Holder, using a PANalytical X'Pert Pro diffractometer, equipped with an X'celerator or a PIXcel detector. The sample was spun during analysis and Cu-radiation was used. The following experimental settings were used:
Tube tension and current: 40 kV, 50 mA
Wavelength alpha1 (CuK$\alpha$1): 1.5406 Å
Wavelength alpha2 (CuK$\alpha$2): 1.5444 Å
Wavelength alpha1 and alpha2 mean (CuK$\alpha$): 1.5418 Å
Start angle [2 theta]: 1-4°
End angle [2 theta]: 30-40°

Analysis time: 50 s ("1 min scan"), 125 s ("2 min scan"), 192 s ("3 min scan"), 397 s ("6 min scan"), 780 s ("13 min scan"), 1020 s ("17 min scan"), 4560 s ("1 h scan")

Unless indicated otherwise, when calculating the peak positions from the XRPD-data, the data was first stripped from the contribution from CuKα2 and was then corrected against an internal standard ($Al_2O_3$).

It is known in the art that an X-ray powder diffraction pattern may be obtained having one or more measurement errors depending on measurement conditions (such as equipment, sample preparation or machine used). In particular, it is generally known that intensities in an XRPD pattern may fluctuate depending on measurement conditions and sample preparation.

For example, persons skilled in the art of XRPD will realise that the relative intensities of peaks may vary according to the orientation of the sample under the test and on the type and setting of the instrument used. The skilled person will also realise that the position of reflections can be affected by the precise height at which the sample sits in the diffractometer and the zero calibration of the diffractometer. The surface planarity of the sample may also have a small effect. Hence a person skilled in the art will appreciate that the diffraction pattern presented herein is not to be construed as absolute and any crystalline form that provides a powder diffraction pattern substantially identical to those disclosed herein fall within the scope of the present disclosure (for further information, see R. Jenkins and R. L. Snyder, "Introduction to X-ray powder diffractomety". John Wiley & Sons, 1996), Thermogravimetric Analysis (TGA)

Approximately 1-5 mg of sample was added to a tared Platinum cup which was then placed in the weighting position of a Perkin-Elmer Pyris 1 TGA analyzer. The furnace was raised and the starting weight of the sample was recorded. The heating program was then started. The sample was heated at a rate of 10° C./min, starting at 25° C. and ending at 90-300° C., depending on where a constant temperature could be attained. The sample was purged with dry nitrogen gas during analysis.

Dynamic Vapor Sorption (DVS)

Approximately 15-20 mg of the sample was weighed into a quartz receptacle, which was then released of static electricity by exposing it to a radioactive source. The quartz receptacle was then positioned in a Surface Measurements System Ltd DVS Advantage instrument. The sample was dried with dry nitrogen gas until a dm/dt below 0.002% per minute was reached. The instrument was running in dm/dt-mode using a dm/dt window of 5 minutes, a minimum stage time of 10 minutes and a maximum stage time of 360 minutes. The sample was then subjected to two consecutive sorption-desorption cycles, using d/m/dt-mode parameters above, and each cycle running from 0-95-0% relative humidity (% RH). One cycle consisted of 20 steps, those between 0-90% RH were taken in 10% RH each.

Differential Scanning Calorimetry (DSC)

Approximately 2 mg of a sample was weighed into an aluminium DSC pan sealed non-hermetically with an aluminium lid (sealed pan). The sample was then loaded into a Perkin-Elmer Diamond DSC cooled and held at 30° C. Once a sufficiently stable heat-flow response was obtained, the sample was heated to 150° C. at a scan rate of 5° C./min and the resulting heat flow response monitored. A nitrogen purge was used to prevent thermally induced oxidation of the sample during heating and also to reduce the thermal lag through the sample to increase the instrument sensitivity. Prior to analysis, the instrument was temperature and heat-flow calibrated using an indium reference standard.

For cryo-DSC experiments, the Perkin-Elmer Diamond DSC was cooled and held at 5° C., and the sample was then analysed from 5 to 200° C. at a scan rate of 10° C./minute.

The starting material 1,1-dioxo-3,3-dibutyl-5-phenyl-7-methylthio-8-(N-{(R)-1'-phenyl-1'-[N-(t-butoxycarbonyl methyl)carbamoyl]methyl}carbamoylmethoxy)-2,3,4,5-tetrahydro-1,5-benzothiazepine can be prepared as described in WO002/50051.

EXAMPLES

Example 1

Preparation of Crystal Modification I

Toluene (11.78 L) was charged to a 20 L round-bottom flask with stirring and 1,1-dioxo-3,3-dibutyl-5-phenyl-7-methylthio-8-(N-{(R)-1'-phenyl-1'-[N'-(t-butoxycarbonyl-methyl)carbamoyl]-methyl}carbamoylmethoxy)-2,3,4,5-tetrahydro-1,5-benzothiazepine (2.94 kg) was added. Formic acid (4.42 L) was added to the reaction mass at 25-30° C. The temperature was raised to 115-120° C. and stirred for 6 hours. The reaction was monitored by HPLC to assure that not more than 1% of the starting material remained in the reaction mass. The reaction mass was cooled to 40-43° C. Purified water (11.78 L) was added while stirring. The reaction mass was further cooled to 25-30° C. and stirred for 15 min. The layers were separated and the organic layer was filtered through a celite bed (0.5 kg in 3 L of toluene) and the filtrate was collected. The celite bed was washed with toluene (5.9 L), the filtrates were combined and concentrated at 38-40° C. under vacuum. The reaction mass was then cooled to 25-30° C. to obtain a solid.

Ethanol (3.7 L) was charged to a clean round-bottom flask with stirring, and the solid obtained in the previous step was added. The reaction mass was heated to 40-43° C. and stirred at this temperature for 30 min. The reaction mass was then cooled to 25-30° C. over a period of 30 min., and then further cooled to 3-5° C. over a period of 2 h, followed by stirring at this temperature for 14 h. Ethanol (3.7 L) was charged to the reaction mass with stirring, while maintaining the temperature at 0-5° C., and the reaction mass was then stirred at this temperature for 1 h. The material was then filtered and washed with ethanol (1.47 L), and vacuum dried for 30 min. The material was dried in a vacuum tray dryer at 37-40° C. for 24 h under nitrogen atmosphere. The material was put in clean double LDPE bags under nitrogen atmosphere and stored in a clean HDPE drum. Yield 1.56 kg.

Crystal modification I has an XRPD pattern, obtained with CuKα1-radiation, with characteristic peaks at ° 2θ positions: 3.1±0.2, 4.4±0.2, 4.9±0.2, 5.2±0.2, 6.0±0.2, 7.4±0.2, 7.6±0.2, 7.8±0.2, 8.2±0.2, 10.0±0.2, 10.5±0.2, 11.3±0.2, 12.4±0.2, 13.3±0.2, 13.5±0.2, 14.6±0.2, 14.9±0.2, 16.0±0.2, 16.6±0.2, 16.9±0.2, 17.2±0.2, 17.7±0.2, 18.0±0.2, 18.3±0.2, 18.8±0.2, 19.2±0.2, 19.4±0.2, 20.1±0.2, 20.4±0.2, 20.7±0.2, 20.9±0.2, 21.1±0.2, 21.4±0.2, 21.8±0.2, 22.0±0.2, 22.3±0.2, 22.9±0.2, 23.4±0.2, 24.0±0.2, 24.5±0.2, 24.8±0.2, 26.4±0.2, '27.1±0.2 and 27.8±0.2. The X-ray powder difractogram is shown in FIG. 4.

Example 2

Preparation of Crystal Modification IV Via EtOH-1

Elobixibat crystal modification I (60 mg) was added to ethanol (1.0 mL) and to a mixture of ethanol and water (0.25+0.75 mL) at 21° C., so as to produce slurries. A stirring bar was then added to each vessel and the vessels were closed. The vessels were left well stirred at 21° C. for one week. The solid residue in each of the experiment vessels was sampled with a Pasteur pipette to a cut Silicon Zero Background Holder, and the samples were analyzed with two consecutive 1-minute XRPD-scans, from 1 to 40° in 2θ. After this one or more slightly longer (3 minutes and 12 seconds) XRPD analysis were performed until two consecutive and identical XRPD-diffractograms had been obtained. When the samples had been analyzed in this way, they were left in the open lab atmosphere for 1 day. Under these conditions (approximately 21° C. and 30% relative humidity) and with the small sample size, ethanol molecules evaporated from the crystal and were replaced by water thereby producing crystal modification IV.

Example 3

Preparation of Crystal Modification IV Via MeOH-1

Approximately 80 mg of elobixibat crystal modification IV was added to a Chromacol vessel and then 1.0 mL of methanol and a stirring flea was added. The vessel was closed with a crimped cap, stirred for a day at 21° C. and was then sampled to a cut Silicon Zero Background Holder (ZBH) and analysed with XRPD repeatedly as the sample dried. When visually dry it was analysed with TGA and was then allowed to absorb moisture from the ambient lab atmosphere before it was re-analysed with XRPD. The XRPD-data on the wet sample is shown in FIG. 8 and after TGA-analysis in FIG. 6.

Example 4

Preparation of Crystal Modification IV Via 1-PrOH-1

99.6 mg of elobixibat crystal modification IV was added to a Chromacol vessel and then 1.0 mL of 1-propanol and a stirring flea was added. The vessel was closed with a crimped cap, stirred for a day at 21° C. and was then sampled to a cut Silicon Zero Background Holder (ZBH) and analysed with XRPD repeatedly as the sample dried. When visually dry it was analysed with TGA and was then allowed to absorb moisture from the ambient lab atmosphere before it was re-analysed with XRPD. The XRPD-data on the wet sample is shown in FIG. 9 and after TGA-analysis is given in FIG. 6.

Example 5

Preparation of Crystal Modification IV Via 2-PrOH-1

103.5 mg of elobixibat crystal modification IV was added to a Chromacol vessel and then 1.0 mL of 2-propanol and a stirring flea was added. The vessel was closed with a crimped cap, stirred for a day at 21° C. and was then sampled to a cut Silicon Zero Background Holder (ZBH) and analysed with XRPD repeatedly as the sample dried. When visually dry it was analysed with TGA and was then allowed to absorb moisture from the ambient lab atmosphere before it was re-analysed with XRPD. The XRPD-data on the wet sample is shown in FIG. 10 and after TGA-analysis is given in FIG. 6.

Example 6

Preparation of Crystal Modification IV

Toluene (145.9 L) and 1,1-dioxo-3,3-dibutyl-5-phenyl-7-methylthio-8-(N-{(R)-t-phenyl-t-[N'-(t-butoxycarbonylm-ethyl)carbamoyl]methyl}carbamoylmethoxy)-2,3,4,5-tetra-hydro-1,5-benzothiazepine (7.295 kg) were charged to a 250-L GLR with stirring under nitrogen atmosphere, and the reaction mass was cooled to 3±2° C. Trifluoroacetic acid (21.89 L) was added slowly to the above reaction mass at 3±2° C. over a period of 2-3 h. The temperature of the reaction mass was raised to 25±5° C. and stirring was continued at this temperature for 21 h. The progress of the reaction was monitored by HPLC.

The reaction mass was cooled to 3±2° C. and purified water (29.18 L) was added at 3±2° C. with stirring over a period of 30-40 min. The reaction mass was then warmed to 25±5° C. and stirred at this temperature for 15 min. The mass was allowed to settle for 15 min. and the layers were separated. The organic layer was washed with water (3×29.18 L) and then with a saturated brine solution (14.59 L). After each washing, the mass was allowed to settle for 15 min before the layer separation. The organic layer was filtered through a stainless steel Nutsche filter over a celite bed (3.0 kg of celite in 17.0 L of toluene) and the filtrate was collected. The celite bed was washed with toluene (14.59 L). The filtrates were combined and concentrated at a temperature below 40° C. under vacuum (500-600 mmHg) to about 7 to 14 L.

The above mass was cooled to 25±5° C. and n-heptane (72.95 L) was added over a period of 10-15 min. The mixture was stirred at 25±5° C. for 2 h and then filtered. The filtered solids were washed with n-heptane (14.59 L) and suction dried for about 30 min.

The above crude compound was dried in a vacuum tray dryer at 38±2° C. (500-600 mm Hg) for 10-12 h. Crude wt: 6.65 kg. Purity by HPLC: 98.5%.

Absolute ethanol (29.18 L) was charged into a 250 L stainless steel reactor and heated to 43±2° C. The crude product from the previous step (6.65 kg) was added to the pre-heated ethanol and stirred at 43±3° C. for 15 min. The resulting solution was then cooled to 25±5° C. and stirred at this temperature for 1 h. During this time, the solution turned turbid.

The mass was seeded with crystal modification IV (2.0 g). The mass was then cooled to 3±2° C. over a period of 2 h, and stirred at this temperature for 10 h. The precipitated solids were filtered and the solids were washed with chilled ethanol (1×3.65 L). The material was suction dried for 30 min. The material was then dried in a vacuum tray drier at 25±5° C. (500-600 mmHg) for 24 h and then at 63±2° C. (~600 mmHg) for ~50 h. The dried product was stored in a HDPE container. Yield 5.31 kg.

The crystals absorbed water from the air. A water content of 2.70% was measured. The crystals were analyzed by XRPD and the results are shown in FIG. 1.

Example 7

Thermal Gravimetric Analysis of Crystal Modification IV

A sample of crystal modification IV was analyzed with XRPD and the water content was checked with TGA. The weight loss for crystal modification IV was initially slow, but accelerated at about 50° C. and was finalized at about 80° C. A weight loss of 2.7% w/w was observed.

Figure 5:
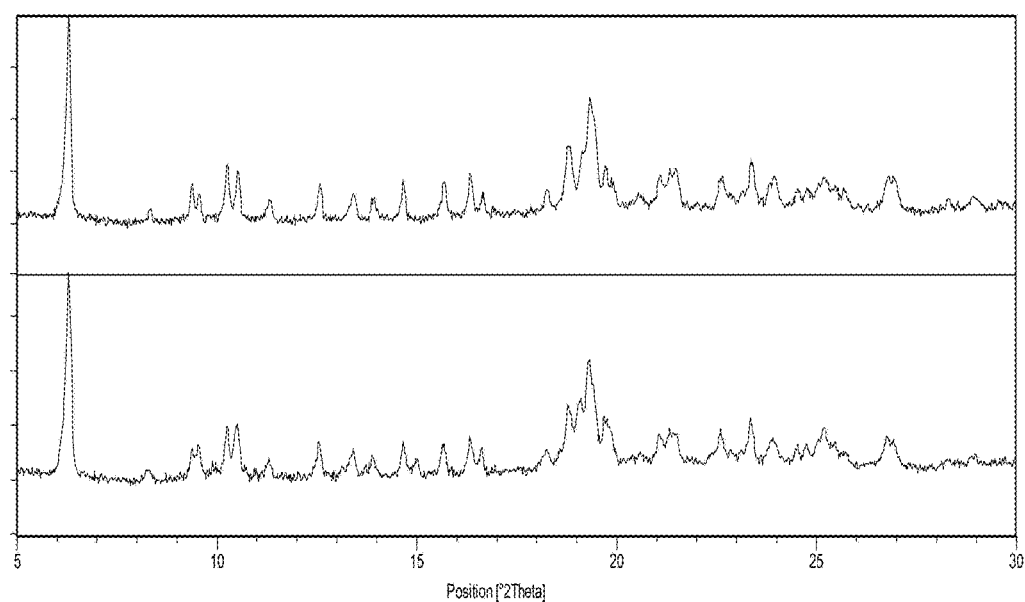
FIG. 5 shows the X-ray powder diffractogram of crystal modification IV before (bottom) and after TGA analysis (top).

The experiment could be repeated several times using the same sample, with rather similar results. Although water had been evaporated from the sample during the TGA analysis, the X-ray powder diffractograms taken before and after TGA analysis were similar (see FIG. 5). This indicates that the absorption of water takes place very rapidly. Furthermore, the experiment shows that the crystal modification is very stable, as the crystal shape is maintained upon evaporation and re-absorption of water.

Example 8

Thermal Gravimetric Analysis of Crystal Modification I

A sample of crystal modification I was analyzed with XRPD and the water content was checked with TGA. The weight loss occurred immediately at the onset of the analysis and was finalized at 50-60° C., indicating that the water in this compound is more loosely bound than in crystal modification IV. A weight loss of 0.99% w/w was observed.

Example 9

DSC analysis of Crystal Modification IV

Crystal modification IV exhibited an endothermic event in the temperature range 45 to 90° C. (onset 56° C.) with a peak at 78° C., with an enthalpy of 66.4 J/g. This event is due to the evaporation of water and corresponds to a water amount of about 2.9% w/w.

A melting peak was observed in the temperature range 95 to 125° C. (onset 103° C.) with a peak at 110° C.

Example 10

Cryo-DSC analysis of crystal modification I

Crystal modification I exhibited an endothermic event in the temperature range 15 to 85° C. (onset 23° C.) with a peak at 56° C., with an enthalpy of 23.2 J/g. This event is due to the evaporation of water and corresponds to a water amount of about 1.03% w/w.

A melting peak was observed in the temperature range 110 to 145° C. (onset 122° C.) with a peak at 131° C.

Example 11

Dynamic Vapor Sorption Analysis of Crystal Modification IV

Figure 11:
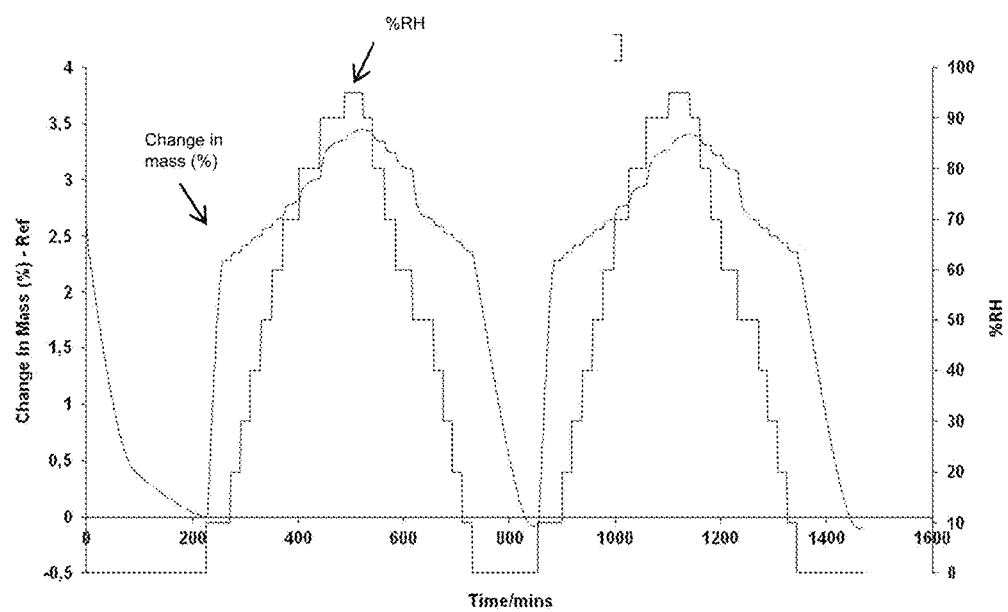
FIG. 11 shows the DVS mass change plot for crystal modification IV. The two curves show the % RH change (right y-axis) and the sample response in weight % (left y-axis). The pre-drying step is shown on the far left of the diagram.

A sample of crystal modification IV was weighed into the quartz scale pan of a Scientific Instruments Dynamic Vapor Sorption instrument. The sample was released of static electricity by moving a radioactive isotope over it and was then put into the instrument. The sample was dried by flushing dry nitrogen gas until the weight was constant and then two consecutive sorption-desorption cycles were run. Crystal modification IV absorbs approximately 2.45% water between 0 and 10% RH, and an additional 0.36 to 0.37% water between 10 and 60% RH. The resulting graph is shown in FIG. 11.

Figure 12A:
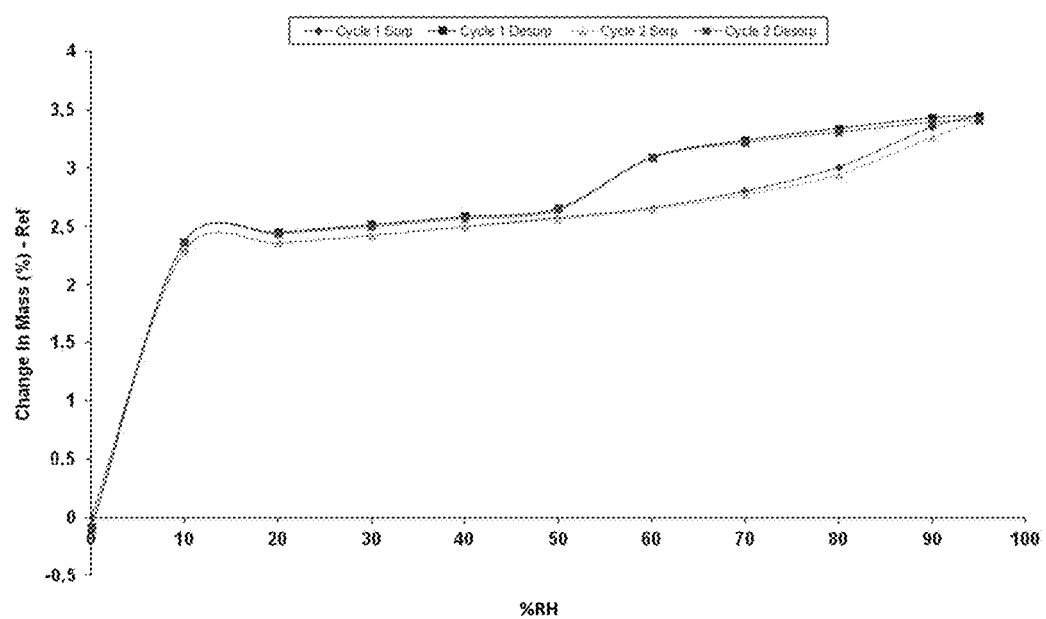
FIGS. 12A and 12B show a plot of water uptake as a function of % RH for crystal modification IV. The sample used in FIG. 12A was obtained from material produced on lab scale, and the sample used in FIG. 12B was obtained from GMP material produced on pilot plant scale.
Figure 12B:
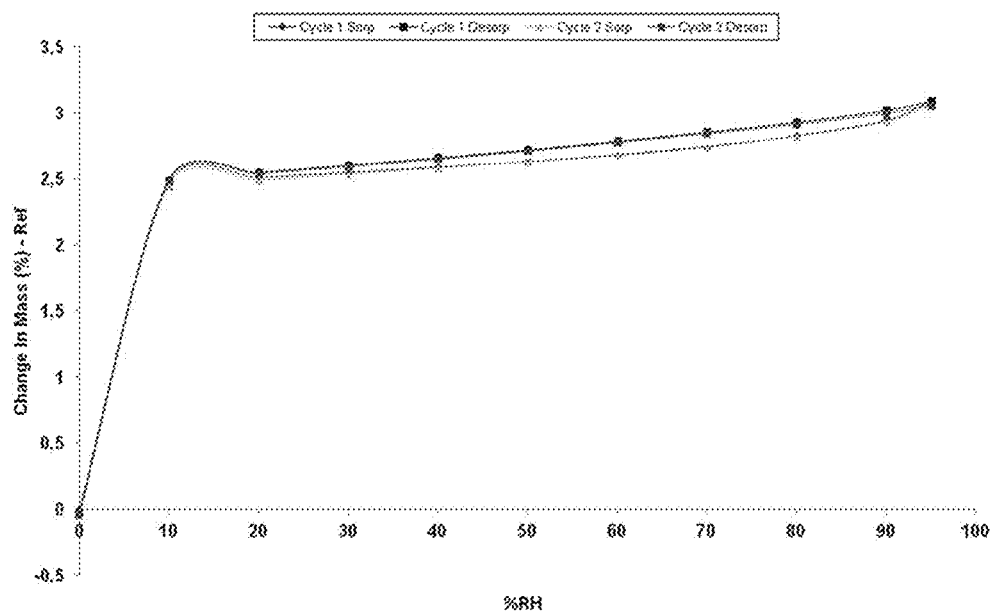

In FIG. 12, a graph of the water uptake as a function of % RH is shown. The sample used in FIG. 12A was obtained from material produced on lab scale, whereas the sample used in FIG. 12B was obtained from GMP material produced on pilot plant scale.

Example 12

Dynamic Vapor Sorption Analysis of Crystal Modification I

Figure 13:
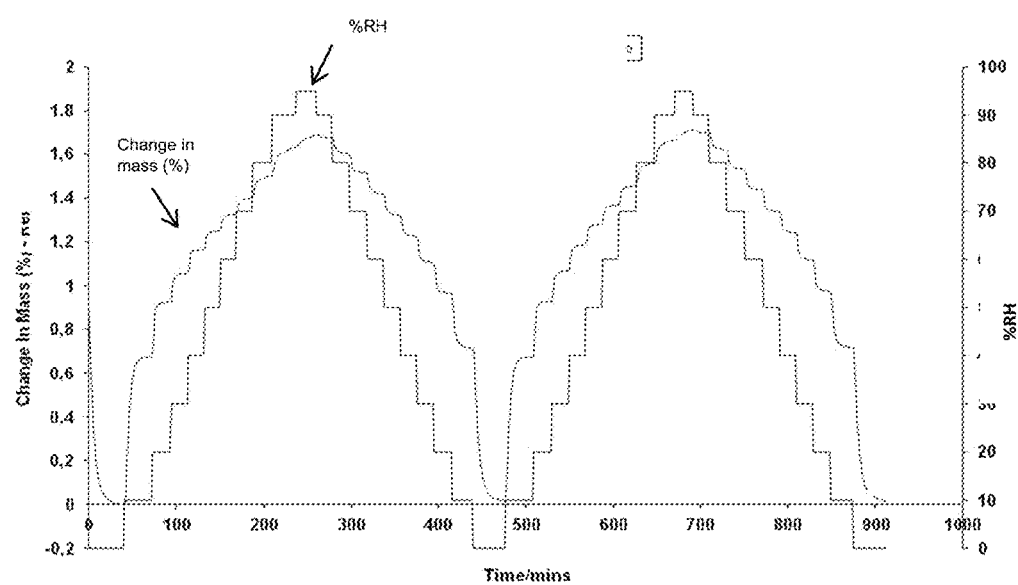
FIG. 13 shows the DVS mass change plot for crystal modification I. The two curves show the % RH change (right y-axis) and the sample response in weight % (left y-axis). The pre-drying step is shown on the far left of the diagram.
Figure 14:
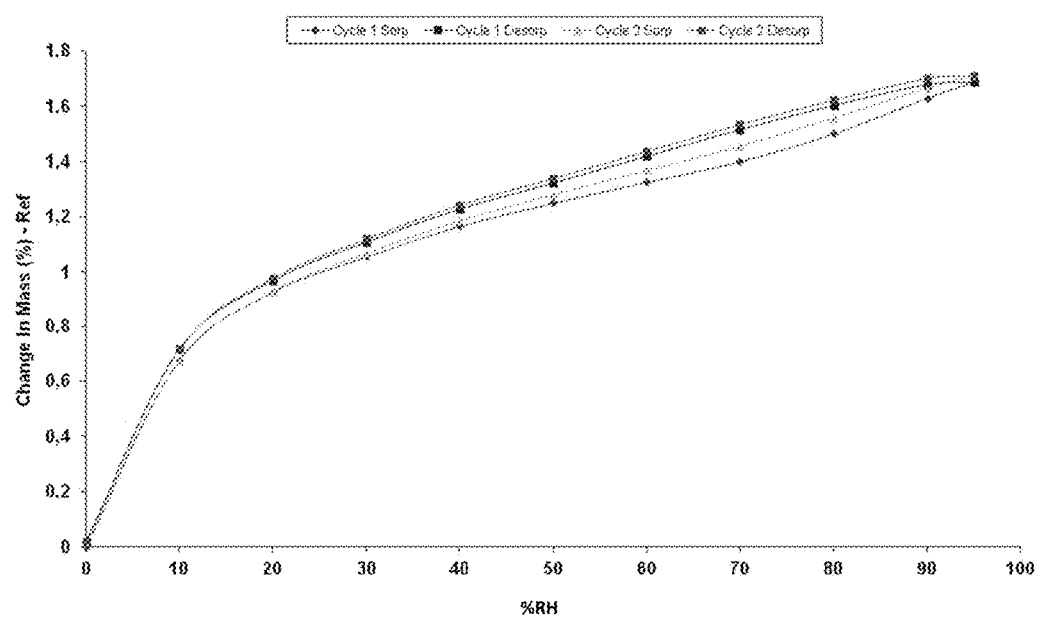
FIG. 14 shows a plot of water uptake as a function of % RH for crystal modification I.

A sample of crystal modification I was weighed into the quarts scale pan of a Scientific Instruments Dynamic Vapor Sorption instrument. The sample was released of static electricity by moving a radioactive isotope over it and was then put into the instrument. The sample was dried by flushing dry nitrogen gas until the weight was constant and then two consecutive sorption-desorption cycles were run. Crystal modification I absorbs approximately 0.66% water between 0 and 10% RH, and an additional 0.65 to 0.69% water between 10 and 60% RH. The resulting graph is shown in FIG. 13. In FIG. 14 a graph of the water uptake as a function of % RH is shown.

Example 13

Stability Test of Crystal Modification IV

A batch of crystal modification IV was stored in a closed glass vial and kept at 20° C. and between 20 and 60% RH for 17 months. XRPD data indicated that the crystalline form was unchanged after 17 months.

Example 14

Micrograph of Crystal Modification IV

Figure 15:
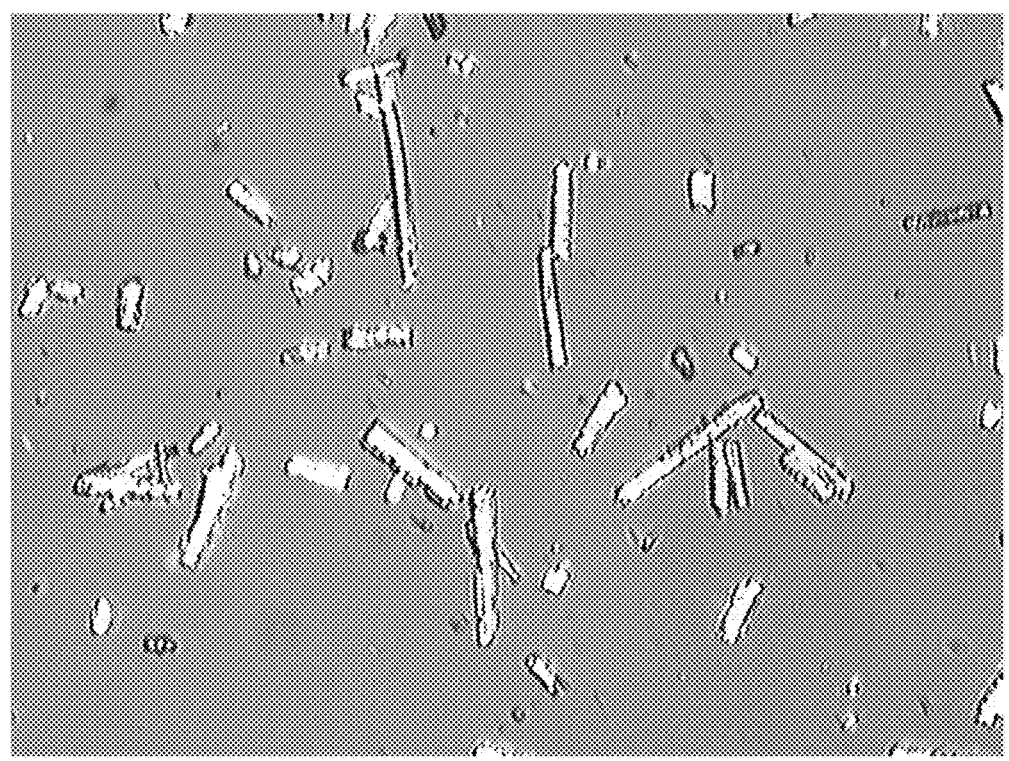
FIG. 15 shows a micrograph of crystal modification IV, taken between slightly uncrossed polarizers and using a 10 times objective.

With a small spatula a small amount of crystal modification IV was put on an objective slide. A drop of Miglyol was added and the solid and liquid were thoroughly mixed with a needle, thus generating a slurry. A cover slip was put on top of the slurry and gently pushed down. The objective slide was then put on the rotating table of a Nikon Optiphot-2 polarized light microscope. The view of the slurry was well focused and the light was then adjusted to Köhler illumination. Then the second polarizer (the analyzer) was inserted perpendicular to the first one (the polarizer) so that the two polarizers were perfectly crossed. The analyzer was then slightly rotated so as to make the two polarizers slightly uncrossed. The specimen was carefully focused and then photographed through a 10 times objective giving FIG. 15.

Example 15

Micrograph of Crystal Modification I

Figure 16:
FIG. 16 shows a micrograph of crystal modification I, taken between slightly uncrossed polarizers and using a 10 times objective.

Following the procedure outlined in Example 14 but using crystal modification I instead, the micrograph shown in FIG. 16 was obtained.

Example 16

Thermal Gravimetric Analysis of Crystal Modification EtOH-1

The solvent content of a sample of EtOH-1 was analyzed with TGA. A weight loss of approximately 6% w/w was observed, indicating that this crystal modification contains one mole of ethanol.

Example 17

High-resolution X-Ray Powder Diffractogram of Elobixibat and Tablets Comprising Crystal Modification I or IV Measurement Method:

X-ray powder diffraction in a high brilliance radiation facility 'SPring-8 26B1'

Detector: R-AXIS V imaging plate detector (Manufacturer: RIGAKU)

Radiation wavelength: 1.0000 Å

Beam size: 100 μm×100 μm

Distance between the sample and the detector: 420 mm

Sample for measurement: enclosed in a glass capillary

Vibrating angle: 80.0°

Exposure time: 80 seconds

Measurement range: 3-15° (2θ)

Measurement temperature: 20° C.

Figure 17:
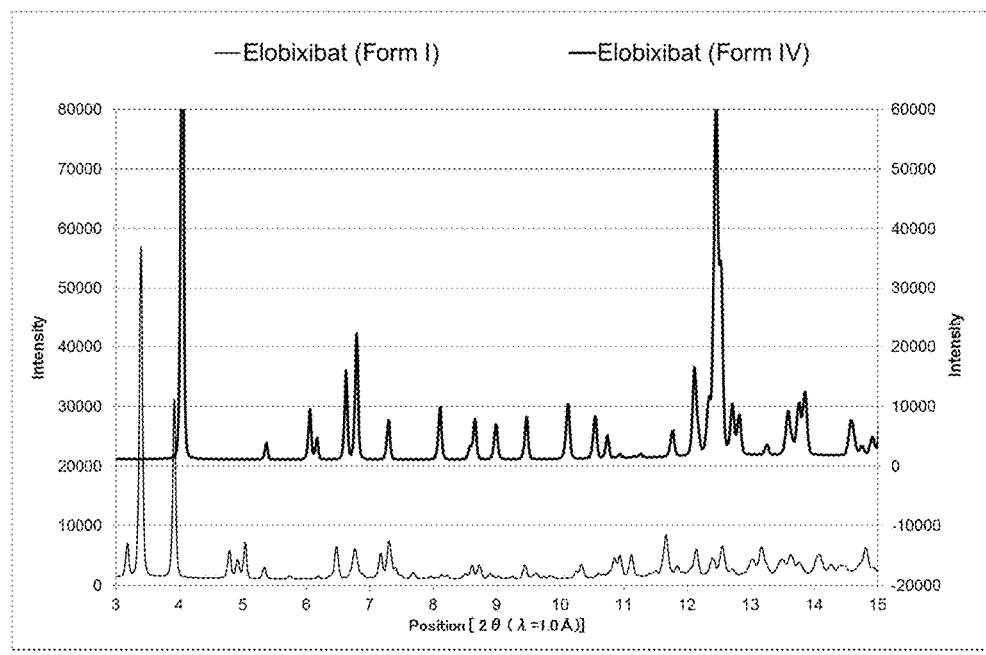
FIG. 17 shows the high-resolution X-ray powder diffractograms of crystal modification I and crystal modification IV.

X-ray powder diffraction measurements by SPring-8 26B1 of crystal modification I (obtained in Example 1) and crystal modification IV were performed. The results are shown in FIG. 17.

Ingredients were mixed in the quantities shown in Table 1. The mixed powers were formed into tables with tabletting machinery (Manesty Betapress) under the condition (Weight: 3.15-3.25 g; Height: 3.85 mm) to obtain tablets comprising crystal modification I, tablets comprising crystal modification IV and placebo tablets, respectively.

TABLE 1

| | Amount/unit (mg) | | |
|---|---|---|---|
| Ingredients | Tablets (cr. mod. I) | Tablets (cr. mod. IV) | Placebo |
| Elobixibat (cr. mod. I) | 15 | — | — |
| Elobixibat (cr. mod. IV) | — | 15 | — |
| Microcrystalline cellulose | 170.42 | 170.42 | 179.42 |
| Mannitol | 113.62 | 113.62 | 119.62 |
| Hypromellose 5 cP | 8.00 | 8.00 | 8.00 |
| Croscarmellose sodium | 8.00 | 8.00 | 8.00 |
| Silica colloidal anhydrous | 1.76 | 1.76 | 1.76 |
| Magnesium stearate | 3.20 | 3.20 | 3.20 |
| Opadry II | 16.0 | 16.0 | 16.0 |

Figure 18:
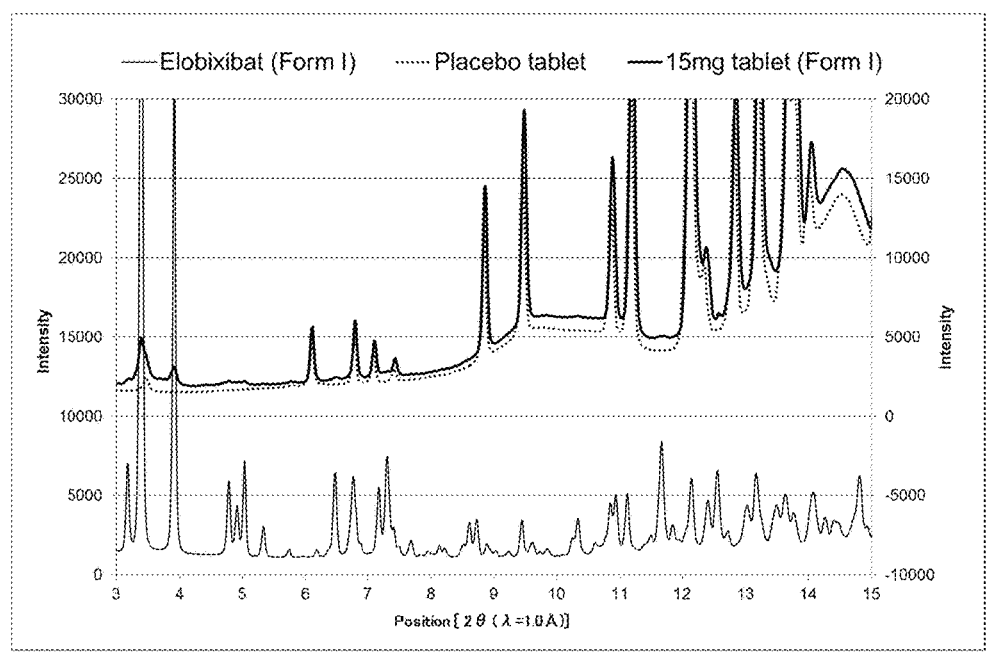
FIG. 18 shows the high-resolution X-ray powder diffractograms of crystal modification I, tablets comprising crystal modification I and placebo tablets.

Tablets comprising crystal modification I were ground to perform X-ray powder diffraction measurement with SPring-8 26B1. In order to identify the diffraction peaks additives other than crystal modification I, X-ray powder diffraction measurement of the placebo tablets was performed with SPring-8 26B1 in the same manner. The characteristic diffraction peaks of tablets comprising crystal modification I were found (FIG. 18).

Figure 19:
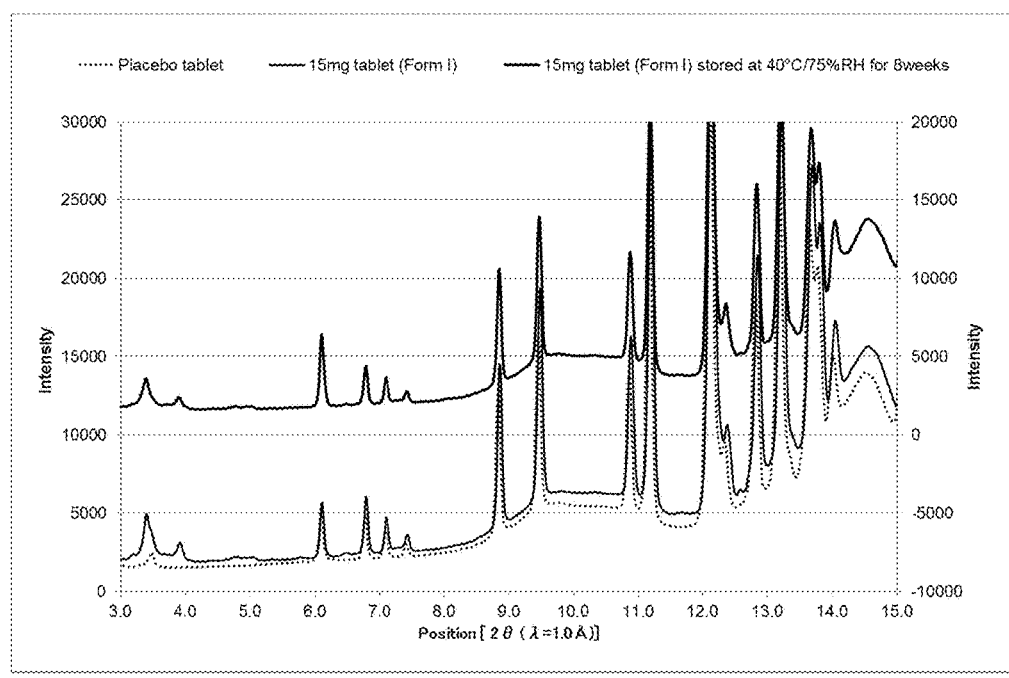
FIG. 19 shows the high-resolution X-ray powder diffractograms of crystal modification I, tablets comprising crystal modification I after 8-week storage under 40° C., 75% relative humidity and placebo tablets.

The tablets were stored under the conditions of 40° C., 75% relative humidity for 8 weeks. Then, X-ray powder diffraction measurement of the stored tablets was performed with SPring-8 26B1 (FIG. 19). No changes were observed in the peaks of the X-ray powder diffractogram, and the characteristic diffraction peaks of the tablets (crystal modification I) were found.

Figure 20:
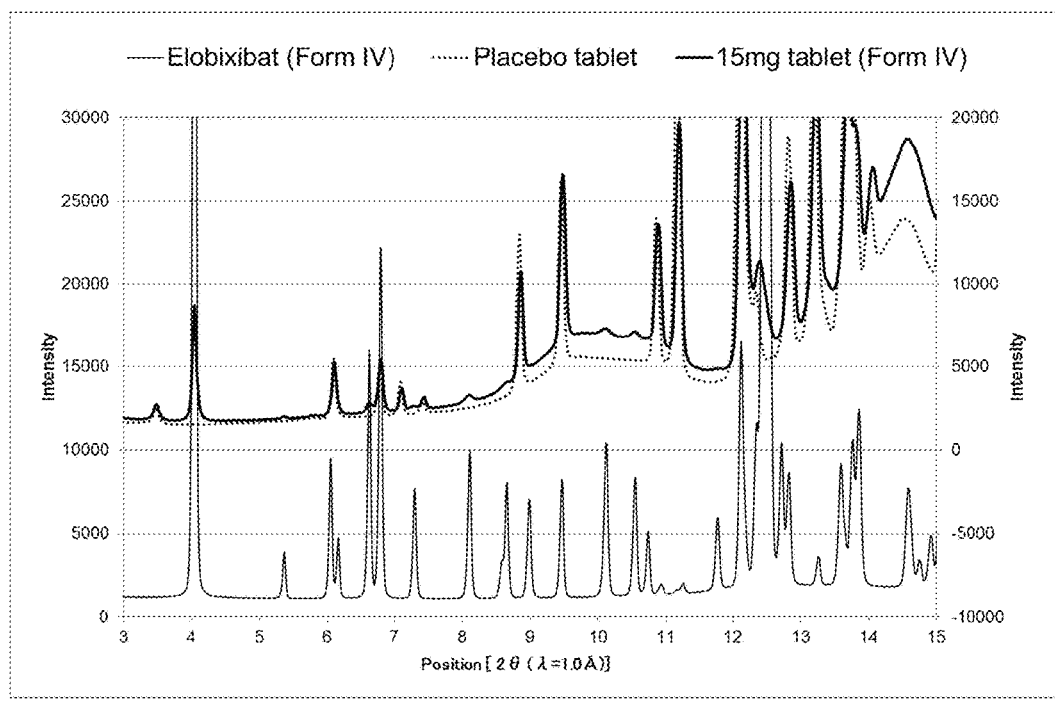
FIG. 20 shows the high-resolution X-ray powder diffractograms of crystal modification IV, tablets comprising crystal modification IV and placebo tablets.

X-ray powder diffraction measurement of crystal modification IV was performed with SPring-8 26B1 in a same manner as above. The characteristic diffraction peaks tablets comprising crystal modification IV were found (FIG. 20).

Figure 21:
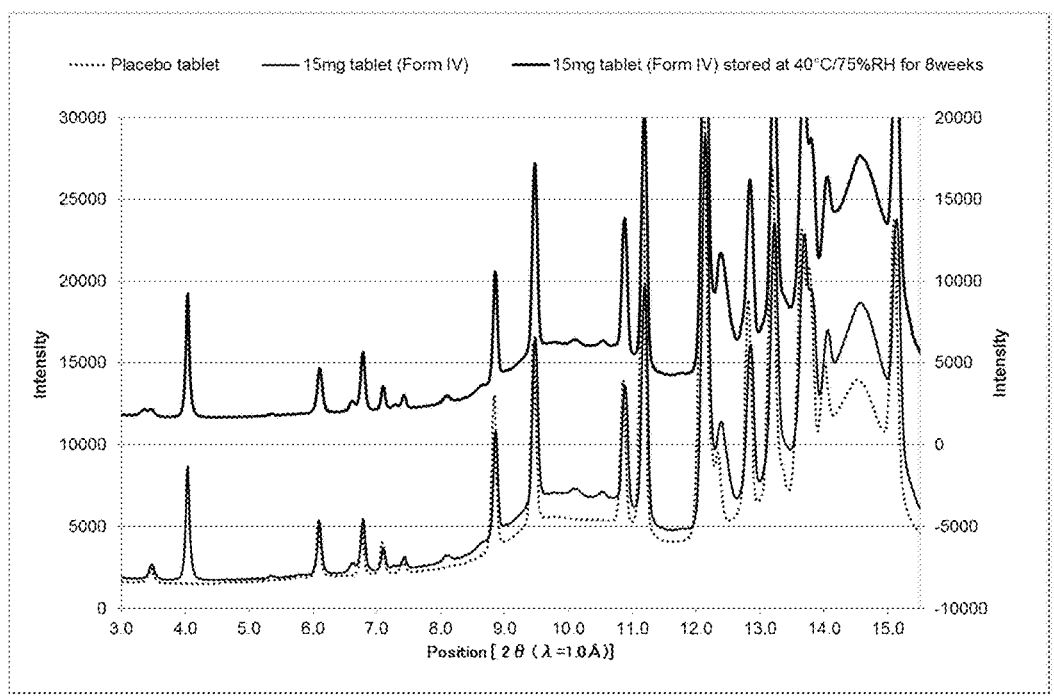
FIG. 21 shows the high-resolution X-ray powder diffractograms of crystal modification IV, tablets comprising crystal modification IV after 8-week storage under 40° C., 75% relative humidity and placebo tablets.

The tablets were stored under the conditions of 40° C., 75% relative humidity for 8 weeks, but no changes were observed in the peaks of the X-ray powder diffractogram; the characteristic diffraction peaks of tablets (crystal modification IV) were found (FIG. 21).

The above results demonstrate that crystal modification IV can exist stably in tablets.

The invention claimed is:

1. Crystal modification EtOH-1 of elobixibat, having an XRPD pattern, obtained with CuKα1-radiation, with peaks at °2θ positions 6.1±0.2 and 18.9±0.2.

2. Crystal modification EtOH-1 of elobixibat according to claim 1, having an XRPD pattern, obtained with CuKα1-radiation, with peaks at °2θ positions 6.1±0.2 and 18.9±0.2 and one or more of peaks: 10.1±0.2, 14.5±0.2, 18.4±0.2, 19.1±0.2, 20.7±0.2, 10.4±0.2, 13.1±0.2, and 11.1±0.2.

3. Crystal modification EtOH-1 of elobixibat according to claim 1, having an XRPD pattern, obtained with CuKα1-radiation, as shown in FIG. 2.

4. Crystal modification MeOH-1 of elobixibat, having an XRPD pattern, obtained with CuKα1-radiation, with peaks at °2θ positions 6.2±0.2 and 18.9±0.2.

5. Crystal modification MeOH-1 of elobixibat according to claim 4, having an XRPD pattern, obtained with CuKα1-radiation, with peaks at °2θ positions 6.2±0.2 and 18.9±0.2 and one or more of peaks: 10.1±0.2, 14.6±0.2, 18.6±0.2, 19.1±0.2, 22.2±0.2, 24.7±0.2, 12.3±0.2, 13.3±0.2, and 16.1±0.2.

6. Crystal modification MeOH-1 of elobixibat according to claim 4, having an XRPD pattern, obtained with CuKα1-radiation, as shown in FIG. 8.

7. Crystal modification 1-PrOH-1 of elobixibat, having an XRPD pattern, obtained with CuKα1-radiation, with peaks at °2θ positions 6.1±0.2 and 19.0±0.2.

8. Crystal modification 1-PrOH-1 of elobixibat according to claim 7, having an XRPD pattern, obtained with CuKα1-radiation, with peaks at °2θ positions 6.1±0.2 and 19.0±0.2 and one or more of peaks: 10.0±0.2, 14.4±0.2, 18.3±0.2, 18.8±0.2, 20.5±0.2, 10.3±0.2, 13.0±0.2, and 11.0±0.2.

9. Crystal modification 1-PrOH-1 of elobixibat according to claim 7, having an XRPD pattern, obtained with CuKα1-radiation, as shown in FIG. 9.

10. Crystal modification 2-PrOH-1 of elobixibat, having an XRPD pattern, obtained with CuKα1-radiation, with peaks at °2θ positions 6.1±0.2 and 19.0±0.2.

11. Crystal modification 2-PrOH-1 of elobixibat according to claim 10, having an XRPD pattern, obtained with CuKα1-radiation, with peaks at °2θ positions 6.1±0.2 and 19.0±0.2 and one or more of peaks: 10.0±0.2, 14.4±0.2, 18.3±0.2, 18.8±0.2, 20.5±0.2, 10.3±0.2, 12.9±0.2, and 11.0±0.2.

12. Crystal modification 2-PrOH-1 of elobixibat according to claim 10, having an XRPD pattern, obtained with CuKα1-radiation, as shown in FIG. 10.

* * * * *